(12) United States Patent
Parenicova

(10) Patent No.: US 8,426,182 B1
(45) Date of Patent: Apr. 23, 2013

(54) ALPHA-AMYLASE

(75) Inventor: Lucie Parenicova, Echt (NL)

(73) Assignee: DSM IP Assets B.V., Heerlen (NL)

(*) Notice: Subject to any disclaimer, the term of this patent is extended or adjusted under 35 U.S.C. 154(b) by 0 days.

(21) Appl. No.: 13/532,072

(22) Filed: Jul. 23, 2012

Related U.S. Application Data

(60) Provisional application No. 61/592,085, filed on Jan. 30, 2012.

(30) Foreign Application Priority Data

Jan. 30, 2012 (EP) .................................... 12153083

(51) Int. Cl.
    *C12N 9/28* (2006.01)
    *C12N 9/26* (2006.01)
    *C12N 15/00* (2006.01)
    *C12N 1/20* (2006.01)
    *C12P 21/06* (2006.01)
    *C07H 21/04* (2006.01)
    *A21D 2/00* (2006.01)
    *A21D 13/00* (2006.01)
    *C07K 1/00* (2006.01)

(52) U.S. Cl.
    USPC ....... 435/202; 435/201; 435/69.1; 435/320.1; 435/252.3; 536/23.1; 536/23.2; 426/20; 426/94; 426/391; 530/350

(58) Field of Classification Search .................. 435/202, 435/201, 69.1, 320.1, 252.3; 536/23.1, 23.2; 426/20, 94, 391; 530/350
See application file for complete search history.

(56) References Cited

U.S. PATENT DOCUMENTS

| | | | |
|---|---|---|---|
| 4,598,048 | A | 7/1986 | Diderichsen et al. |
| 4,604,355 | A | 8/1986 | Outtrup |
| RE38,507 | E | 4/2004 | Olesen |

FOREIGN PATENT DOCUMENTS

WO     2008148845 A2     12/2008

OTHER PUBLICATIONS

Cherry, Jr. et al., "DNA Encoding a Maltogenic Alpha Amylase," Database Geneseq, Retrieved from EBI Accession No. GSN: AAZ10579, (Nov. 17, 1999).
Pedersen et al., "Bacillus Maltogenic Amylase Coding Sequence," Database Geneseq, Retrieved from EBI Accession No. GSN: AAf62389, (Nov. 5, 2001).
Imperio et al., *Alicyclobacillus pohliae* SP. NOV., A Thermophilic, Endospore-Forming Bacterium Isolated From Geothermal Soil of the North-West Slope of Mount Melbourne (Antarctica), International Journal of Systematic and Evolutionary Microbiology, vol. 58, No. Pt 1, pp. 221-225, (Jan. 2008).
Extended European Search Report for EP12153083 Date of Completion: Mar. 15, 2012.

*Primary Examiner* — Ganapathirama Raghu
(74) *Attorney, Agent, or Firm* — Baker Donelson Bearman, Caldwell & Berkowitz, PC

(57) ABSTRACT

This invention relates to an alpha-amylase, a process for its preparation and the use of the amylase. The invention relates to a newly identified polynucleotide sequence from *Alicyclobacillus pohliae* comprising a gene that encodes the alpha-amylase enzyme. The invention features the full-length coding sequence of the gene as well as the amino acid sequence of the full-length functional protein of the gene. The invention also relates to methods of using these proteins in industrial processes, for example in food industry, such as the baking industry. Also included in the invention are cells transformed with a polynucleotide according to the invention suitable for producing these proteins and cells.

21 Claims, 5 Drawing Sheets

5'-
ATGAAAAAGAAAACGCTTTCATTATTTGTGGGACTGATGCTGCTCCTCGGTCTTCTG
TTCAGCGGTTCTCTTCCGTACAATCCAAACGCCGCTGAAGCCAGCAGTTCCGCAAG
CGTCAAAGGGGACGTGATTTACCAGATTATCATTGACCGGTTTTACGATGGGGACA
CGACGAACAACAATCCTGCCAAAAGTTATGGACTTTACGATCCCACCAAATCGAAG
TGGAAAATGTATTGGGGCGGGGATCTGGAGGGGGTTCGTCAAAAACTTCCTTATCT
TAAACAGCTGGGCGTAACGACGATCTGGTTGTCCCCGGTTTTGGACAATCTGGATA
CACTTGCAGGTACCGATAACACTGGCTATCACGGATACTGGACGCGCGATTTTAAA
CAGATTGAGGAACATTTCGGGAATTGGACCACATTTGACACGTTGGTCAATGATGC
TCACCAAAACGGAATCAAGGTGATTGTCGACTTTGTGCCCAATCATTCAACTCCTTT
TAAGGCAAACGATTCCACCTTTGCGGAAGGCGGCGCCCTCTACGACAACGGAACC
TATATGGGCAATTATTTTGATGACGCAACAAAAGGGTACTTTCACCATAATGGGGAC
ATCAGCAACTGGGACGACCGGTACGAGGCGCAATGGAAAAACTTCACGGATCCAG
CCGGTTTCTCGCTTGCCGATTTGTCGCAGGAAAATGGCACGATTGCTCAATACCTG
ACCGATGCGGCGGTTCAATTAGTAGCACATGGAGCGGATGGTTTGCGGATTGATG
CGGTGAAGCATTTTAATTCTGGGTTCTCCAAATCGTTGGCTGATAAACTGTACCAAA
AGAAAGACATTTTCCTAGTGGGGGAATGGTACGGAGATGACCCCGGAGCAGCCAA
TCATTTGGAAAAGGTCCGGTACGCCAACAACAGCGGTGTCAATGTGCTGGATTTTG
ATCTCAACACGGTGATTCGAAATGTGTTCGGTACATTTACGCAAACGATGTACGATC
TTAACAATATGGTGAACCAAACGGGGAACGAGTACAAATACAAAGAAAATCTAATCA
CATTTATCGATAACCATGATATGTCGAGATTTCTTACGGTAAATTCGAACAAGGCGA
ATTTGCACCAGGCGCTTGCTTTCATTCTCACTTCGCGGGGAACGCCCTCCATCTAT
TACGGAACCGAACAATACATGGCAGGCGGCAATGACCCGTACAACAGGGGGATGA
TGCCGGCGTTTGATACGACAACCACCGCCTTTAAAGAGGTGTCAACTCTGGCGGG
GTTGCGCAGGAACAATGCAGCGATCCAGTACGGCACCACCACCCAACGTTGGATC
AACAATGATGTTTACATTTATGAGCGGAAATTTTTCAACGATGTCGTATTGGTGGCC
ATCAATCGAAACACGCAATCCTCCTACTCGATTTCCGGTTTGCAGACTGCCTTGCCA
AATGGCAACTATGCGGATTATCTGTCAGGGCTGTTGGGGGGGAACGGGATTTCCG
TTTCCAATGGAAGTGTCGCTTCGTTCACGCTTGCGCCTGGAGCCGTGTCTGTTTGG
CAGTACAGCACATCCGCTTCAGCGCCGCAAATCGGATCGGTTGCTCCGAATATGG
GAATTCCGGGTAATGTGGTCACGATCGACGGGAAGGTTTTGGAACGACGCAGGG
AACCGTGACATTTGGCGGAGTGACAGCGACTGTAAAATCCTGGACATCAAACCGGA
TTGAAGTGTACGTGCCCAACATGGCCGCCGGTCTGACCGATGTAAAAGTCACCGC
GGGTGGAGTTTCCAGCAATCTGTATTCTTACAATATTTTGAGTGGAACGCAGACATC
GGTTGTGTTTACTGTGAAAAGTGCTCCTCCGACCAACCTGGGGGATAAGATTTACC
TGACGGGCAACATACCGGAATTGGGAAATTGGAGCACGGATACGAGCGGAGCCGT
TAACAATGCGCAAGGGCCCCTGCTCGCGCCCAATTATCCGGATTGGTTTTATGTAT
TCAGCGTTCCGGCAGGAAAGACGATTCAATTCAAGTTTTTCATCAAGCGTGCGGAT
GGAACGATTCAATGGGAGAATGGTTCGAACCACGTGGCCACAACTCCCACGGGTG
CAACCGGTAACATCACTGTCACGTGGCAAAACTAG
-3'

Fig. 3

```
MKKKTLSLFVGLMLLLGLLFSGSLPYNPNAAEASSSASVKGDVIYQIIIDRFYDGDTTNN
NPAKSYGLYDPTKSKWKMYWGGDLEGVRQKLPYLKQLGVTTIWLSPVLDNLDTLAGT
DNTGYHGYWTRDFKQIEEHFGNWTTFDTLVNDAHQNGIKVIVDFVPNHSTPFKANDST
FAEGGALYDNGTYMGNYFDDATKGYFHHNGDISNWDDRYEAQWKNFTDPAGFSLAD
LSQENGTIAQYLTDAAVQLVAHGADGLRIDAVKHFNSGFSKSLADKLYQKKDIFLVGEW
YGDDPGAANHLEKVRYANNSGVNVLDFDLNTVIRNVFGTFTQTMYDLNNMVNQTGNE
YKYKENLITFIDNHDMSRFLTVNSNKANLHQALAFILTSRGTPSIYYGTEQYMAGGNDPY
NRGMMPAFDTTTTAFKEVSTLAGLRRNNAAIQYGTTTQRWINNDVYIYERKFFNDVVLV
AINRNTQSSYSISGLQTALPNGNYADYLSGLLGGNGISVSNGSVASFTLAPGAVSVWQY
STSASAPQIGSVAPNMGIPGNVVTIDGKGFGTTQGTVTFGGVTATVKSWTSNRIEVYVP
NMAAGLTDVKVTAGGVSSNLYSYNILSGTQTSVVFTVKSAPPTNLGDKIYLTGNIPELGN
WSTDTSGAVNNAQGPLLAPNYPDWFYVFSVPAGKTIQFKFFIKRADGTIQWENGSNHV
ATTPTGATGNITVTWQN
```

Fig. 4

```
5'-
ATGAAGAAGAAAACACTTTCTCTATTTGTCGGTTTGATGCTGCTGCTTGGTTTGCTG
TTCTCTGGTTCACTTCCTTACAACCCGAATGCAGCTGAGGCTTCTTCAAGTGCAAGT
GTGAAGGGAGATGTGATTTACCAAATCATCATCGACCGTTTCTATGACGGTGACAC
AACAAACAACAATCCGGCAAAATCATACGGCCTGTATGATCCGACAAAAAGCAAAT
GGAAAATGTACTGGGGCGGAGATCTTGAAGGCGTTCGCCAAAAGCTGCCATATTTG
AAGCAGCTTGGTGTAACGACGATTTGGCTTTCGCCTGTTCTTGACAATCTTGATACG
CTGGCAGGTACTGACAATACAGGTTATCACGGCTACTGGACAAGAGATTTCAAACA
AATCGAAGAGCATTTCGGAAACTGGACGACATTTGACACACTTGTGAATGATGCTC
ACCAAAACGGCATCAAAGTGATCGTTGATTTCGTTCCGAATCACAGCACGCCATTC
AAAGCAAACGACAGCACGTTTGCAGAAGGCGGTGCTTTGTACGATAACGGTACTTA
CATGGGAAATTATTTTGATGATGCAACAAAAGGCTATTTCCATCATAACGGAGATAT
CAGCAACTGGGATGACCGTTATGAAGCACAATGGAAAAACTTCACAGATCCTGCTG
GCTTCAGCCTTGCTGATTTATCACAAGAAAACGGAACGATCGCTCAATATTTAACTG
ACGCTGCTGTTCAGCTTGTTGCTCACGGTGCTGACGGCCTTCGCATTGATGCAGTG
AAGCACTTCAACAGCGGCTTCAGCAAAAGCCTTGCTGACAAGCTGTATCAAAAGAA
GGATATTTTCCTTGTCGGTGAATGGTATGGAGATGACCCAGGTGCTGCTAATCACC
TTGAAAAAGTGCGTTATGCAAACAACTCTGGTGTAAATGTGCTTGATTTTGATTTGA
ATACGGTTATCCGCAATGTATTCGGAACATTTACACAAACGATGTACGATTTAAACA
ACATGGTGAACCAAACAGGAAATGAATACAAATATAAAGAAAACCTGATTACATTTA
TTGACAACCATGATATGAGCCGCTTCCTGACTGTAAACAGCAACAAAGCAAACCTTC
ATCAGGCACTTGCTTTTATTTTAACTTCAAGAGGAACACCGTCAATTTACTACGGAA
CAGAACAATATATGGCAGGCGGAAATGATCCATACAACCGCGGCATGATGCCTGCT
TTTGATACAACAACAACTGCATTCAAAGAAGTATCAACGCTTGCAGGGCTGCGTCG
TAATAATGCAGCAATTCAATACGGCACAACAACTCAGCGCTGGATCAACAATGATGT
ATACATATATGAAAGAAAATTCTTTAATGATGTTGTGCTTGTTGCAATCAACCGAAAT
ACACAATCTTCTTATTCCATCAGCGGCCTTCAAACGGCACTGCCAAACGGAAACTA
CGCTGATTACCTTTCCGGCCTGCTTGGCGGAAACGGAATTTCTGTCAGCAACGGTT
CTGTTGCATCATTTACGCTTGCTCCTGGTGCTGTTTCTGTTTGGCAATATTCAACTT
CAGCTTCTGCTCCTCAAATCGGTTCTGTTGCACCGAATATGGGTATCCCGGGAAAC
GTTGTGACGATTGACGGAAAAGGCTTCGGAACGACACAAGGTACTGTAACATTCGG
CGGCGTTACTGCAACTGTAAAAAGCTGGACATCAAACCGTATTGAAGTGTATGTGC
CGAATATGGCTGCTGGCCTGACTGATGTAAAAGTGACAGCTGGCGGTGTTTCTTCA
AACCTATACTCTTACAACATTTTATCAGGCACACAAACATCTGTTGTATTCACTGTAA
AATCAGCACCGCCGACAAACCTAGGTGACAAGATTTACTTAACAGGAAACATCCCT
GAGCTTGGAAACTGGAGCACTGATACAAGCGGAGCTGTTAACAATGCACAAGGCC
CGCTTCTTGCACCGAATTATCCGGACTGGTTTTATGTATTCTCTGTTCCTGCTGGAA
AAACGATTCAATTCAAATTCTTTATCAAACGCGCTGACGGAACGATTCAATGGGAAA
ACGGTTCAAACCATGTGGCAACAACTCCAACTGGTGCAACAGGAAATATCACTGTT
ACTTGGCAGAATTAA
-3'
```

Fig. 5

SEQUENCE LISTING

<160> NUMBER OF SEQ ID NOS: 4

<210> SEQ ID NO 1
<211> LENGTH: 2160
<212> TYPE: DNA

<213> ORGANISM: Alicyclobacillus pohliae

<400> SEQUENCE: 1

```
atgaaaaaga aaacgctttc attatttgtg ggactgatgc tgctcctcgg tcttctgttc      60
agcggttctc ttccgtacaa tccaaacgcc gctgaagcca gcagttccgc aagcgtcaaa     120
ggggacgtga tttaccagat tatcattgac cggttttacg atggggacac gacgaacaac     180
aatcctgcca aaagttatgg actttacgat cccaccaaat cgaagtggaa atgtattgg      240
ggcggggatc tggagggggt tcgtcaaaaa cttccttatc ttaaacagct gggcgtaacg     300
acgatctggt tgtccccggt tttggacaat ctggatacac ttgcaggtac cgataacact     360
ggctatcacg gatactggac gcgcgatttt aaacagattg aggaacattt cgggaattgg     420
accacatttg acgttggt caatgatgct caccaaaacg gaatcaaggt gattgtcgac       480
tttgtgccca atcattcaac tccttttaag gcaaacgatt ccacctttgc ggaaggcggc     540
gccctctacg acaacggaac ctatatgggc aattattttg atgacgcaac aaaagggtac     600
tttcaccata atggggacat cagcaactgg gacgaccggt acgaggcgca atggaaaaac     660
ttcacggatc cagccggttt ctcgcttgcc gatttgtcgc aggaaaatgg cacgattgct     720
caatacctga ccgatgcggc ggttcaatta gtagcacatg gagcggatgg tttgcggatt     780
gatgcggtga agcattttaa ttctgggttc tccaaatcgt tggctgataa actgtaccaa     840
agaaagaca ttttcctagt gggggaatgg tacggagatg accccggagc agccaatcat     900
ttggaaaagg tccggtacgc caacaacagc ggtgtcaatg tgctggattt tgatctcaac     960
acggtgattc gaaatgtgtt cggtacattt acgcaaacga tgtacgatct taacaatatg    1020
gtgaaccaaa cggggaacga gtacaaatac aaagaaaatc taatcacatt tatcgataac    1080
catgatatgt cgagatttct tacggtaaat tcgaacaagg cgaatttgca ccaggcgctt    1140
gctttcattc tcacttcgcg gggaacgccc tccatctatt acggaaccga acaatacatg    1200
gcaggcggca atgacccgta caacaggggg atgatgccgg cgtttgatac gacaaccacc    1260
gcctttaaag aggtgtcaac tctggcgggg ttgcgcagga acaatgcagc gatccagtac    1320
ggcaccacca cccaacgttg gatcaacaat gatgtttaca tttatgagcg gaaatttttc    1380
aacgatgtcg tattggtggc catcaatcga aacacgcaat cctcctactc gatttccggt    1440
ttgcagactg ccttgccaaa tgcaactat gcggattatc tgtcagggct gttgggggg      1500
aacgggattt ccgtttccaa tggaagtgtc gcttcgttca cgcttgcgcc tggagccgtg    1560
tctgtttggc agtacagcac atccgcttca gcgccgcaaa tcggatcggt tgctccgaat    1620
atgggaattc cggtaatgt ggtcacgatc gacgggaaag gttttggaac gacgcaggga    1680
accgtgacat ttggcggagt gacagcgact gtaaaatcct ggacatcaaa ccggattgaa    1740
gtgtacgtgc caacatggc cgccggtctg accgatgtaa aagtcaccgc gggtggagtt    1800
tccagcaatc tgtattctta caatattttg agtggaacgc agacatcggt tgtgtttact    1860
gtgaaaagtg ctcctccgac caacctgggg gataagattt acctgacggg caacataccg    1920
gaattgggaa attggagcac ggatacgagc ggagccgtta caatgcgca agggcccctg     1980
ctcgcgccca attatccgga ttggttttat gtattcagcg ttccggcagg aaagacgatt    2040
caattcaagt ttttcatcaa gcgtgcggat ggaacgattc aatgggagaa tggttcgaac    2100
cacgtggcca caactcccac gggtgcaacc ggtaacatca ctgtcacgtg gcaaaactag    2160
```

<210> SEQ ID NO 2
<211> LENGTH: 719
<212> TYPE: PRT

-continued

<213> ORGANISM: Alicyclobacillus pohliae

<400> SEQUENCE: 2

Met Lys Lys Lys Thr Leu Ser Leu Phe Val Gly Leu Met Leu Leu Leu
1               5                   10                  15

Gly Leu Leu Phe Ser Gly Ser Leu Pro Tyr Asn Pro Asn Ala Ala Glu
            20                  25                  30

Ala Ser Ser Ser Ala Ser Val Lys Gly Asp Val Ile Tyr Gln Ile Ile
        35                  40                  45

Ile Asp Arg Phe Tyr Asp Gly Asp Thr Thr Asn Asn Asn Pro Ala Lys
50                  55                  60

Ser Tyr Gly Leu Tyr Asp Pro Thr Lys Ser Lys Trp Lys Met Tyr Trp
65                  70                  75                  80

Gly Gly Asp Leu Glu Gly Val Arg Gln Lys Leu Pro Tyr Leu Lys Gln
                85                  90                  95

Leu Gly Val Thr Thr Ile Trp Leu Ser Pro Val Leu Asp Asn Leu Asp
            100                 105                 110

Thr Leu Ala Gly Thr Asp Asn Thr Gly Tyr His Gly Tyr Trp Thr Arg
        115                 120                 125

Asp Phe Lys Gln Ile Glu Glu His Phe Gly Asn Trp Thr Thr Phe Asp
130                 135                 140

Thr Leu Val Asn Asp Ala His Gln Asn Gly Ile Lys Val Ile Val Asp
145                 150                 155                 160

Phe Val Pro Asn His Ser Thr Pro Phe Lys Ala Asn Asp Ser Thr Phe
                165                 170                 175

Ala Glu Gly Gly Ala Leu Tyr Asp Asn Gly Thr Tyr Met Gly Asn Tyr
            180                 185                 190

Phe Asp Asp Ala Thr Lys Gly Tyr Phe His His Asn Gly Asp Ile Ser
        195                 200                 205

Asn Trp Asp Asp Arg Tyr Glu Ala Gln Trp Lys Asn Phe Thr Asp Pro
210                 215                 220

Ala Gly Phe Ser Leu Ala Asp Leu Ser Gln Glu Asn Gly Thr Ile Ala
225                 230                 235                 240

Gln Tyr Leu Thr Asp Ala Ala Val Gln Leu Val Ala His Gly Ala Asp
                245                 250                 255

Gly Leu Arg Ile Asp Ala Val Lys His Phe Asn Ser Gly Phe Ser Lys
            260                 265                 270

Ser Leu Ala Asp Lys Leu Tyr Gln Lys Lys Asp Ile Phe Leu Val Gly
        275                 280                 285

Glu Trp Tyr Gly Asp Asp Pro Gly Ala Ala Asn His Leu Glu Lys Val
290                 295                 300

Arg Tyr Ala Asn Asn Ser Gly Val Asn Val Leu Asp Phe Asp Leu Asn
305                 310                 315                 320

Thr Val Ile Arg Asn Val Phe Gly Thr Phe Thr Gln Thr Met Tyr Asp
                325                 330                 335

Leu Asn Asn Met Val Asn Gln Thr Gly Asn Glu Tyr Lys Tyr Lys Glu
            340                 345                 350

Asn Leu Ile Thr Phe Ile Asp Asn His Asp Met Ser Arg Phe Leu Thr
        355                 360                 365

Val Asn Ser Asn Lys Ala Asn Leu His Gln Ala Leu Ala Phe Ile Leu
370                 375                 380

Thr Ser Arg Gly Thr Pro Ser Ile Tyr Tyr Gly Thr Glu Gln Tyr Met
385                 390                 395                 400

Ala Gly Gly Asn Asp Pro Tyr Asn Arg Gly Met Met Pro Ala Phe Asp

```
                    405                 410                 415
Thr Thr Thr Thr Ala Phe Lys Glu Val Ser Thr Leu Ala Gly Leu Arg
            420                 425                 430

Arg Asn Asn Ala Ala Ile Gln Tyr Gly Thr Thr Gln Arg Trp Ile
        435                 440                 445

Asn Asn Asp Val Tyr Ile Tyr Glu Arg Lys Phe Phe Asn Asp Val Val
450                 455                 460

Leu Val Ala Ile Asn Arg Asn Thr Gln Ser Ser Tyr Ser Ile Ser Gly
465                 470                 475                 480

Leu Gln Thr Ala Leu Pro Asn Gly Asn Tyr Ala Asp Tyr Leu Ser Gly
            485                 490                 495

Leu Leu Gly Gly Asn Gly Ile Ser Val Ser Asn Gly Ser Val Ala Ser
                500                 505                 510

Phe Thr Leu Ala Pro Gly Ala Val Ser Val Trp Gln Tyr Ser Thr Ser
            515                 520                 525

Ala Ser Ala Pro Gln Ile Gly Ser Val Ala Pro Asn Met Gly Ile Pro
        530                 535                 540

Gly Asn Val Val Thr Ile Asp Gly Lys Gly Phe Gly Thr Thr Gln Gly
545                 550                 555                 560

Thr Val Thr Phe Gly Gly Val Thr Ala Thr Val Lys Ser Trp Thr Ser
                565                 570                 575

Asn Arg Ile Glu Val Tyr Val Pro Asn Met Ala Ala Gly Leu Thr Asp
            580                 585                 590

Val Lys Val Thr Ala Gly Gly Val Ser Ser Asn Leu Tyr Ser Tyr Asn
        595                 600                 605

Ile Leu Ser Gly Thr Gln Thr Ser Val Val Phe Thr Val Lys Ser Ala
610                 615                 620

Pro Pro Thr Asn Leu Gly Asp Lys Ile Tyr Leu Thr Gly Asn Ile Pro
625                 630                 635                 640

Glu Leu Gly Asn Trp Ser Thr Asp Thr Ser Gly Ala Val Asn Asn Ala
            645                 650                 655

Gln Gly Pro Leu Leu Ala Pro Asn Tyr Pro Asp Trp Phe Tyr Val Phe
        660                 665                 670

Ser Val Pro Ala Gly Lys Thr Ile Gln Phe Lys Phe Ile Lys Arg
    675                 680                 685

Ala Asp Gly Thr Ile Gln Trp Glu Asn Gly Ser Asn His Val Ala Thr
        690                 695                 700

Thr Pro Thr Gly Ala Thr Gly Asn Ile Thr Val Thr Trp Gln Asn
705                 710                 715

<210> SEQ ID NO 3
<211> LENGTH: 2160
<212> TYPE: DNA
<213> ORGANISM: Artificial Sequence
<220> FEATURE:
<223> OTHER INFORMATION: Sets out the artificial codon pair optimized
      polynucleotide sequence from Alicyclobacillus pohliae NCIMB14276
      encoding the alpha-amylase according to the invention

<400> SEQUENCE: 3
atgaagaaga aaacactttc tctatttgtc ggtttgatgc tgctgcttgg tttgctgttc      60
tctggttcac ttccttacaa cccgaatgca gctgaggctt cttcaagtgc aagtgtgaag    120
ggagatgtga tttaccaaat catcatcgac cgtttctatg acggtgacac aacaaacaac    180
aatccggcaa atcatacgg cctgtatgat ccgacaaaaa gcaaatggaa atgtactgg      240 ggcggagatc ttgaaggcgt tcgccaaaag ctgccatatt tgaagcagct tggtgtaacg    300
```

```
acgatttggc tttcgcctgt tcttgacaat cttgatacgc tggcaggtac tgacaataca      360
ggttatcacg gctactggac aagagatttc aaacaaatcg aagagcattt cggaaactgg      420
acgacatttg acacacttgt gaatgatgct caccaaaacg gcatcaaagt gatcgttgat      480
ttcgttccga atcacagcac gccattcaaa gcaaacgaca gcacgtttgc agaaggcggt      540
gctttgtacg ataacggtac ttacatggga aattattttg atgatgcaac aaaaggctat      600
ttccatcata acggagatat cagcaactgg gatgaccgtt atgaagcaca atggaaaaac      660
ttcacagatc ctgctggctt cagccttgct gatttatcac aagaaaacgg aacgatcgct      720
caatatttaa ctgacgctgc tgttcagctt gttgctcacg gtgctgacgg ccttcgcatt      780
gatgcagtga agcacttcaa cagcggcttc agcaaaagcc ttgctgacaa gctgtatcaa      840
aagaaggata ttttccttgt cggtgaatgg tatgagatg acccaggtgc tgctaatcac      900
cttgaaaaag tgcgttatgc aaacaactct ggtgtaaatg tgcttgattt tgatttgaat      960
acggttatcc gcaatgtatt cggaacattt acacaaacga tgtacgattt aaacaacatg     1020
gtgaaccaaa caggaaatga atacaaatat aaagaaaacc tgattacatt tattgacaac     1080
catgatatga gccgcttcct gactgtaaac agcaacaaag caaaccttca tcaggcactt     1140
gctttatttt aacttcaag aggaacaccg tcaatttact acggaacaga acaatatatg     1200
gcaggcggaa atgatccata caaccgcggc atgatgcctg cttttgatac aacaacaact     1260
gcattcaaag aagtatcaac gcttgcaggg ctgcgtcgta ataatgcagc aattcaatac     1320
ggcacaacaa ctcagcgctg atcaacaat gatgtataca tatatgaaag aaaattcttt     1380
aatgatgttg tgcttgttgc aatcaaccga atacacaat cttcttattc catcagcggc     1440
cttcaaacgg cactgccaaa cggaaactac gctgattacc tttccggcct gcttggcgga     1500
aacggaattt ctgtcagcaa cggttctgtt gcatcattta cgcttgctcc tggtgctgtt     1560
tctgtttggc aatattcaac ttcagcttct gctcctcaaa tcggttctgt tgcaccgaat     1620
atgggtatcc cgggaaacgt tgtgacgatt gacggaaaag gcttcggaac gacacaaggt     1680
actgtaacat tcggcggcgt tactgcaact gtaaaaagct ggacatcaaa ccgtattgaa     1740
gtgtatgtgc cgaatatggc tgctggcctg actgatgtaa aagtgacagc tggcggtgtt     1800
tcttcaaacc tatactctta acacatttta tcaggcacac aaacatctgt tgtattcact     1860
gtaaaatcag cacccgccgac aaacctaggt gacaagattt acttaacagg aaacatccct     1920
gagcttggaa actggagcac tgatacaagc ggagctgtta acaatgcaca aggcccgctt     1980
cttgcaccga attatccgga ctggttttat gtattctctg ttcctgctgg aaaaacgatt     2040
caattcaaat tctttatcaa acgcgctgac ggaacgattc aatgggaaaa cggttcaaac     2100
catgtggcaa caactccaac tggtgcaaca ggaaatatca ctgttacttg gcagaattaa     2160
```

<210> SEQ ID NO 4
<211> LENGTH: 100
<212> TYPE: DNA
<213> ORGANISM: Artificial Sequence
<220> FEATURE:
<223> OTHER INFORMATION: An amyQ terminator and a PmeI restriction site
      were introduced in the pBHA12 vector by digesting pBHA12 with SphI
      and HindIII and cloning this sequence

<400> SEQUENCE: 4

```
gcatgcgttt aaacaaaaac acctccaagc tgagtgcggg tatcagcttg gaggtgcgtt       60
tattttttca gccgtatgac aaggtcggca tcagaagctt                            100
```

ALPHA-AMYLASE

This application claims priority to European Application No. 12153083.6, filed Jan. 30, 2012; and U.S. Provisional Application No. 61/592,085, filed Jan. 30, 2012, the content of both of which are incorporated herein by reference in their entireties.

FIELD OF INVENTION

This invention involves a novel alpha-amylase, a process for its preparation and the use of the amylase.

The invention relates to a newly identified polynucleotide sequence comprising a gene that encodes the novel alpha-amylase enzyme. The invention features the full length coding sequence of the novel gene as well as the amino acid sequence of the full-length functional protein of the gene. The invention also relates to methods of using these proteins in industrial processes, for example in food industry, such as the baking industry. Also included in the invention are cells transformed with a polynucleotide according to the invention suitable for producing these proteins and cells. The invention relates to a method of manufacturing the polynucleotide according to the invention. The invention further relates to a method for manufacturing the polypeptide according to the invention.

BACKGROUND OF THE INVENTION

Studies on bread staling have indicated that the starch fraction in bread recrystallizes during storage, thus causing an increase in crumb firmness, which may be measured as an increase in hardness of bread slices.

The present invention relates to an alpha-amylase. Alpha-amylases have been used in industry for a long time.

Alpha-amylases have traditionally been provided through the inclusion of malted wheat or barley flour and give several advantages to the baker. Alpha-amylase is used to give satisfactory gas production and gas retention during dough leavening and to give satisfactory crust color. This means that if this enzyme is not used in sufficient amount, the volume, texture, and appearance of the loaf are substantially impaired. Alpha-amylase occurs naturally within the wheat crop itself, measured routinely by Hagberg Falling Number (ICC method 107), and steps are taken to minimise such variations by the addition of alpha-amylase at the mill and through the use of specialty ingredients at the bakery as the enzyme is of such critical importance.

In more recent times, alpha-amylase from cereal has been largely replaced with enzymes from microbial sources, including fungal and bacterial sources. Through use of biotechnology in strain selection, fermentation and processing, enzymes can be prepared from such microbial sources and this brings advantage over malt flour because the enzyme is of more controlled quality, relatively pure and more cost effective in use. The properties of alpha-amylases, and their technological effects, do however show important differences. Besides giving influence to gas production, gas retention and crust color, alpha-amylase can have bearing on the shelf-life of the baked product. Starch within the wheat flour contains two principal fractions, amylose and amylopectin, and these are organised in the form of starch granules. A proportion of these granules from hard-milling wheat varieties become "damaged", with granules splitting apart as a consequence of the energy of milling. In the process of baking, the starch granules gelatinise; this process involves a swelling of the granule by the uptake of water and a loss of the crystalline nature of the granule; in particular amylopectins within the native granule are known to exist as crystallites and these molecules dissociate and lose crystallinity during gelatinisation. Once the bread has been baked, amylopectin recrystallises slowly over a numbers of days and it is this recrystallisation, or retrogradation of starch, that is regarded as being the principal cause of bread staling. These varying forms of the starch and their interaction with alpha-amylase dictate the role the enzyme has with respect to baking technology. Alpha-amylase from fungal sources, most typically coming from Aspergillus species, acts principally on damaged starch during the mixing of dough and throughout fermentation/proof. The low heat stability of the enzyme means that the enzyme is inactivated during baking and, critically before starch gelatinisation has taken place, such that there is little or no breakdown of the starch from the undamaged fraction. As a consequence, fungal amylase is useful in providing sugars for fermentation and color, but has practically no value in extending shelf-life. Bacterial alpha-amylase, most typically from Bacillus amyloliquifaciens, on the other hand does bring extended temperature stability and activity during the baking of bread and while starch is undergoing gelatinisation. Bacterial amylase then leads to more extensive modification of the starch and, in turn, the qualities of the baked bread; in particular the crumb of the baked bread can be perceptibly softer throughout shelf-life and can permit the shelf-life to be increased. However, while bacterial alpha-amylase can be useful with regard to shelf-life extension, it is difficult to use practically as small over-doses lead to an unacceptable crumb structure of large and open pores, while the texture can become too soft and "gummy".

The inventor has identified an alpha amylase from a particular bacterial source that has a thermostability falling inbetween typical fungal and bacterial alpha amylases. The thermostability of this enzyme is higher than fungal alpha amylase, thereby allowing greater activity on amylopectin during and after gelatinisation, but it is not acting as long into the baking process as the typical bacterial amylases and is not over digesting the starch.

U.S. Pat. No. 4,598,048 describes the preparation of a maltogenic amylase enzyme. U.S. Pat. No. 4,604,355 describes a maltogenic amylase enzyme, preparation and use thereof. U.S. RE38,507 describes an antistaling process and agent. The product described in U.S. RE38,507 is used in industry under the trade name NOVAMYL® antistaling agent.

It was set out to find an organism able to produce an improved alpha-amylase. As a result the inventor has identified the Alicyclobacillus pohliae NCIMB14276 strain which was discovered in the Antarctic. This is a new strain, it was not previously used as a source for an alpha-amylase which has improved properties.

SUMMARY OF THE INVENTION

The present invention relates to polypeptides. The invention provides a novel alpha-amylase that may be used for retarding staling of baked products such as bread and cake. The invention further provides novel polynucleotides encoding the novel alpha-amylase enzyme.

Accordingly, the invention relates to:
a polynucleotide encoding for a polypeptide having alpha-amylase activity comprising:
(a) a polynucleotide sequence encoding a polypeptide having an amino acid sequence as set out in SEQ ID NO: 2 or having an amino acid sequence as set out in amino acids 34 to 719 of SEQ ID NO: 2; or (b) a polynucleotide sequence encoding a polypeptide having at least 99.5% identity to a polypeptide having an amino acid sequence as set out in amino acids 34 to 719 of SEQ ID NO: 2; or
(c) a polynucleotide sequence as set out in nucleotides 100 to 2157 of SEQ ID NO: 1 or SEQ ID NO: 3; or
(d) a polynucleotide sequence as set out in SEQ ID NO: 1 or SEQ ID NO: 3.

Further the invention concerns:
an alpha-amylase polypeptide comprising:
(a) an amino acid sequence as set out in amino acids 34 to 719 of SEQ ID NO: 2; or
(b) an amino acid sequence having at least 99.5% identity to an amino acid sequence as set out in amino acids 34 to 719 of SEQ ID NO: 2: or
(c) an amino acid sequence encoded by a polynucleotide as set out in nucleotides 100 to 2157 of SEQ ID NO: 1 or SEQ ID NO: 3; or
(d) the amino acid sequence according to (c), wherein the polynucleotide is produced by *Alicyclobacillus pohliae* NCIMB 14276.

In another aspect the invention relates to a vector comprising the polynucleotide sequence according to the invention. The invention also relates to a recombinant host cell comprising the polynucleotide according to the invention. The invention relates to a method of manufacturing the polynucleotide according to the invention. The invention further relates to a method for manufacturing the polypeptide according to the invention. The invention relates to the use of said polypeptide in food manufacturing. The invention also relates to an enzyme composition. The invention also relates to a method to prepare a dough and to a dough comprising the polypeptide according to the invention or the enzyme composition according to the invention.

The invention also relates to a method to prepare a baked product comprising the step of baking the dough according to the invention.

The invention further relates to a baked product.

The invention further relates to a method to produce a polypeptide comprising the use of *Alicyclobacillus pohliae* NCIMB14276.

BRIEF DESCRIPTION OF THE DRAWINGS

FIG. 3 Sets out SEQ ID NO: 1.
FIG. 4 Sets out SEQ ID NO: 2.
FIG. 5 Sets out SEQ ID NO: 3.

BRIEF DESCRIPTION OF THE SEQUENCE LISTING

Figure 1:
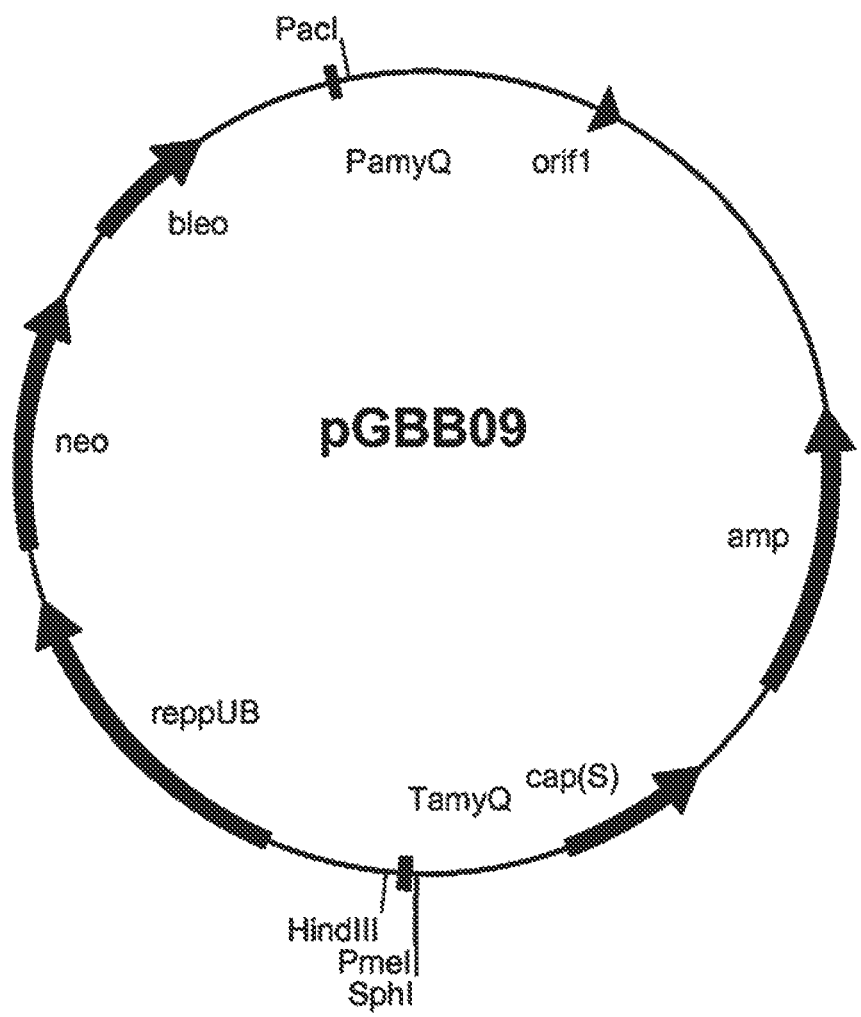
FIG. 1 sets out the plasmid map of pGBB09.

SEQ ID NO: 1 sets out the polynucleotide sequence from *Alicyclobacillus pohliae* NCIMB14276 encoding the wild type signal sequence (set out in nucleotides 1 to 99), the alpha-amylase according to the invention (set out in nucleotides 100 to 2157), and a stop codon at the 3'-terminus (set out in nucleotides 2157 to 2160).

SEQ ID NO: 2 sets out the amino acid sequence of the *Alicyclobacillus pohliae* NCIMB14276 wild type signal sequence (set out in amino acids 1 to 33) and the alpha-amylase according to the Invention (set out in amino acids 34 to 719). Also referred to herein as DSM-AM protein.

SEQ ID NO: 3 sets out a codon optimised polynucleotide sequence from *Alicyclobacillus pohliae* NCIMB 14276 encoding the wild type signal sequence (set out in nucleotides 1 to 99), the alpha-amylase according to the invention (set out in nucleotides 100 to 2157), and a stop codon at the 3'-terminus (set out in nucleotides 2157 to 2160).

DETAILED DESCRIPTION OF THE INVENTION

Throughout the present specification and the accompanying claims the words "comprise" and "include" and variations such as "comprises", "comprising", "includes" and "including" are to be interpreted as open and inclusive. That is, these words are intended to convey the possible inclusion of other elements or integers not specifically recited, where the context allows.

Throughout the present specification and the accompanying claims the wording "nucleotides 100 to 2157" means nucleotides 100 up to and including 2157. Throughout the present specification and the accompanying claims the wording "amino acids 34 to 719" means amino acids 34 up to and including 719.

The terms "polypeptide having an amino acid sequence as set out in amino acids 34 to 719 of SEQ ID NO: 2, "the mature polypeptide as set out in SEQ ID NO: 2" and "mature DSM-AM" are used interchangeably herein.

The terms "polypeptide having at least 99.5% identity to a polypeptide having an amino acid sequence as set out in amino acids 34 to 719 of SEQ ID NO: 2", "mature polypeptide according to the invention", "mature enzyme according to the invention", "amylolytic enzyme according to the invention", "alpha-amylase enzyme according to the invention", "alpha-amylase according to the invention" and "polypeptide according to the invention" are used interchangeably herein.

The terms "according to the invention" and "of the invention" are used interchangeably herein.

The terms "DSM-AM gene", "alpha-amylase gene according to the invention", "AM gene" and "polynucleotide according to SEQ ID NO: 1" are used interchangeably herein. The term "polynucleotide according to the invention" includes SEQ ID NO: 1 and SEQ ID NO: 3.

In the context of the present invention "mature polypeptide" is defined herein as a polypeptide having alpha-amylase activity that is in its final form following translation and any post-translational modifications, including N-terminal processing, C-terminal truncation, glycosylation, phosphorylation, etc. The process of maturation may depend on the particular expression vector used, the expression host and the production process.

To confirm the polynucleotide sequence of the DSM-AM gene from the *Alicyclobacillus pohliae* NCIMB14276, the whole genome of *A. pohliae* NCIMB14276 was sequenced. The results hereof confirmed the polynucleotide, encoding the DSM-AM protein, is as disclosed in SEQ ID NO: 1. From this the 719 amino acid sequence of the DSM-AM protein as set out in SEQ ID NO: 2 was confirmed. The first 33 amino acids, starting from the N'-terminus of the DSM-AM protein, belong to the signal sequence.

Polynucleotides

The invention relates to a polynucleotide encoding for a polypeptide having alpha-amylase activity comprising:
(a) a polynucleotide sequence encoding a polypeptide having an amino acid sequence as set out in amino acids 34 to 719 of SEQ ID NO: 2; or
(b) a polynucleotide sequence encoding a polypeptide having at least 99.5% identity to a polypeptide having an amino acid sequence as set out in amino acids 34 to 719 of SEQ ID NO: 2; or
(c) a polynucleotide sequence as set out in nucleotides 100 to 2157 of SEQ ID NO: 1 or SEQ ID NO: 3; or (d) a polynucleotide sequence as set out SEQ ID NO: 1 or SEQ ID NO: 3.

In an aspect, a polynucleotide of the invention is an isolated polynucleotide comprising:
(a) a polynucleotide sequence as set out in nucleotides 100 to 2157 of the polynucleotide sequence of SEQ ID NO: 1 or 3 (inclusive of nucleotides 100 and 2157, for the avoidance of doubt); or
(b) a polynucleotide sequence encoding a polypeptide having an amino acid sequence as set out in SEQ ID NO: 2 or having an amino acid sequence as set out in amino acids 34 to 719 of SEQ ID NO: 2 (inclusive of amino acids 34 and 719, for the avoidance of doubt); or
(c) a polynucleotide sequence as set out in SEQ ID NO:1 or SEQ ID NO:3.

In one aspect such isolated polynucleotide can be obtained synthetically, e.g. by solid phase synthesis or by other methods known to the person skilled in the art.

The sequences according to SEQ ID NO: 1 and SEQ ID NO: 3 include the nucleotides encoding the mature polypeptide according to the invention and the wild type signal sequence. SEQ ID NO: 2 includes the mature polypeptide according to the invention and the wild type signal sequence.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is obtained. Thus, in one embodiment, an isolated polynucleotide includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated polynucleotide fragment" is a polynucleotide fragment that is not naturally occurring as a fragment and would not be found in the natural state.

Polynucleotides of the invention also include polynucleotides which comprise certain variant sequences of the coding sequence of SEQ ID NO: 1 or 3 and which can encode a functional alpha-amylase. Such variant sequences thus encode polypeptides with alpha-amylase activity.

A polynucleotide sequence of the invention will generally comprise sequence encoding a polypeptide having at least about 99.5% sequence identity to a polypeptide having an amino acid sequence as set out in amino acids 34 to 719 of SEC) ID NO: 2 as calculated over the full lengths of those sequences.

The coding sequence of SEQ ID NO: 1 or 3 may be modified by nucleotide substitutions. The polynucleotide of SEQ ID NO: 1 or 3 may alternatively or additionally be modified by one or more insertions and/or deletions and/or by an extension at either or both ends. The modified polynucleotide encodes a polypeptide which has alpha-amylase activity.

In an embodiment of the polynucleotide according to the invention the polynucleotide is produced by *Alicyclobacillus pohliae* NCIMB314276. As used herein, the terms "polynucleotide" or "nucleic acid molecule" and the like are intended to include DNA molecules (e.g., cDNA or genomic DNA) and RNA molecules (e.g., mRNA) and analogs of the DNA or RNA generated using nucleotide analogs. The polynucleotide molecule can be single-stranded or double-stranded, but preferably is double-stranded DNA. The polynucleotide may be synthesized so that it includes synthetic or modified nucleotides. A number of different types of modification to polynucleotides are known in the art. These include methylphosphonate and phosphorothioate backbones, addition of acridine or polylysine chains at the 3' and/or 5' ends of the molecule. Such oligonucleotides can be used, for example, to prepare polynucleotides that have altered base-pairing abilities or increased resistance to nucleases.

For the purposes of the present invention, it is to be understood that the polynucleotides described herein may be modified by any method available in the art. Such modifications may be carried out, for example to increase the extent to which a polynucleotide of the invention may be expressed in a suitable host cell.

A polynucleotide of the invention, such as a DNA polynucleotide, may be produced recombinantly, synthetically, or by any means available to those of skill in the art. They may also be cloned by standard techniques. A polynucleotide of the invention is typically provided in isolated and/or purified form.

Polynucleotides may be produced using recombinant means, for example using PCR (polymerase chain reaction) cloning techniques. This will involve making a pair of primers (e.g. of about 15-30 nucleotides) to a region of the polynucleotide which it is desired to amplify, bringing the primers into contact with mRNA or cDNA obtained from a suitable cell, performing a polymerase chain reaction under conditions which bring about amplification of the desired region, isolating and recovering the amplified DNA. The primers may be designed to contain suitable restriction enzyme recognition sites so that the amplified DNA can conveniently be cloned into a suitable cloning vector.

Such techniques may be used to obtain all or part of the polynucleotide of SEQ ID NO: 1 or 3 described herein or variants thereof.

Polynucleotides which do not have 100% sequence identity to the sequence of SEQ ID NO: 1 or 3 but which nevertheless fall within the scope of the invention may be obtained in a number of ways. For example, polynucleotides may be obtained by an appropriate mutagenesis technique, such as site-directed mutagenesis of SEQ ID NO: 1 or 3. This may be useful where, for example, silent codon changes are required to sequences to optimize codon preferences for a particular host cell in which the polynucleotide sequences are being expressed. Other sequence changes may be desired in order to introduce restriction enzyme recognition sites, or to alter the property or function of the polypeptides encoded by the polynucleotides.

To increase the likelihood that the Introduced enzyme is expressed in active form in a cell of the invention, the corresponding encoding nucleotide sequence may be adapted to optimise its codon usage to that of the chosen host cell, for example SEQ ID NO: 3. Several methods for codon optimisation are known in the art. A preferred method to optimise codon usage of the nucleotide sequences to that of the chosen host cell is a codon pair optimization technology as disclosed in WO20061077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

As a simple measure for gene expression and translation efficiency, herein, the Codon Adaptation Index (CAI), as described in Xuhua Xia, Evolutionary Bioinformatics 2007, 3: 53-58, is used. The index uses a reference set of highly expressed genes from a species to assess the relative merits of each codon, and a score for a gene is calculated from the frequency of use of all codons in that gene. The index assesses the extent to which selection has been effective in moulding the pattern of codon usage. In that respect it is useful for predicting the level of expression of a gene, for assessing the adaptation of viral genes to their hosts, and for making comparisons of codon usage in different organisms. The index may also give an approximate indication of the likely success of heterologous gene expression. In the codon pair optimized genes according to the invention, the CAI is 0.6 or more, 0.7 or more, 0.8 or more, 0.85 or more, 0.87 or more 0.90 or more, 0.95 or more, or about 1.0.

The invention further provides double stranded polynucleotides comprising a polynucleotide of the invention and its complement.

Polynucleotides, probes or primers of the invention may carry a revealing label. Suitable labels include radioisotopes such as $^{32}$P or $^{35}$S, enzyme labels, or other protein labels such as biotin. Such labels may be added to polynucleotides, probes or primers of the invention and may be detected using techniques known per se.

Polypeptides

The invention provides an (isolated) polypeptide having starch degrading activity. The invention further relates to a method for manufacturing the polypeptide according to the invention.

The terms "peptide" and "oligopeptide" are considered synonymous (as is commonly recognized) and each term can be used interchangeably as the context requires to indicate a chain of at least two amino acids coupled by peptidyl linkages. The word "polypeptide" (or protein) is used herein for chains containing more than seven amino acid residues. All oligopeptide and polypeptide formulas or sequences herein are written from left to right and in the direction from amino terminus to carboxy terminus. The three-letter code of amino acids used herein is commonly known in the art and can be found in Sambrook, at al. (*Molecular Cloning: A Laboratory Manual*, 3$^{rd}$ ed., Cold Spring Harbor Laboratory Press, Cold Spring Harbor, N.Y., 2001).

The invention relates to an alpha-amylase polypeptide comprising:
  (a) an amino acid sequence as set out in amino acids 34 to 719 of SEQ ID NO: 2; or
  (b) an amino acid sequence having at least 99.5% identity to an amino acid sequence as set out in amino acids 34 to 719 of SEQ ID NO: 2; or
  (c) an amino acid sequence encoded by a polynucleotide as set out in nucleotides 100 to 2157 of SEQ ID NO: 1 or SEQ ID NO; 3.

In an embodiment, the invention relates to an isolated polypeptide comprising:
  (a) amino acid sequence as set out in amino acids 34 to 719 of SEQ ID NO: 2; or or
  (b) an amino acid sequence encoded by a polynucleotide as set out in nucleotides 100 to 2157 of SEQ ID NO: 1 or 3; or
  (c) the amino acid sequence according to (b), wherein the polynucleotide is produced by *Alicyclobacillus pohliae* NCIMB14276; or
  (d) an amino acid sequence encoded by a polynucleotide sequence as set out in SEQ ID NO: 1 or SEQ ID NO: 3.

The polypeptide of the invention comprises the amino acid sequence having at least 99.5% identity, preferably at least 99.6% identity, preferably at least 99.7% identity preferably at least 99.8% identity, preferably at least 99.9% identity to a polypeptide having an amino acid sequence as set out in amino acids 34 to 719 of SEQ ID NO: 2 which has alpha-amylase activity. In general, the naturally occurring amino acid sequence shown in amino acids 34 to 719 of SEQ ID NO: 2 is preferred.

As is known to the person skilled in the art it is possible that the N- and/or C-termini of SEQ ID NO: 2 or of the mature polypeptide in the amino acid sequence according to SEQ ID NO: 2 (as set out in amino acids 34 to 719) might be heterogeneous, due to variations in processing during maturation. In particular such processing variations might occur upon overexpression of the polypeptide. In addition, exo-protease activity might give rise to heterogeneity. The extent to which heterogeneity occurs depends also on the host and fermentation protocols that are used. Such C-terminual processing artefacts might lead to shorter polypeptides or longer polypeptides as indicated with SEQ ID NO: 2 or with the mature polypeptide in the amino acid sequence according to SEQ ID NO: 2. As a result of such processing variations the N-terminus might also be heterogeneous. Processing variants at the N-terminus could be due to alternative cleavage of the signal sequence by signal peptidases.

In a further aspect, the invention provides an isolated polynucleotide encoding the polypeptide according to SEQ ID NO: 2 or of the mature polypeptide in the amino acid sequence according to SEQ ID NO: 2 which contain additional residues and start at position −1, or −2, or −3 etc. Alternatively, it might lack certain residues and as a consequence start at position 2, or 3, or 4 etc. Also additional residues may be present at the C-terminus, e.g. at position 720, 721 etc. Alternatively, the C-terminus might lack certain residues and as a consequence end at position 718, or 717 etc.

The polypeptide of the invention preferably has at 99.5% sequence identity to the sequence set out in SEQ ID NO: 2.

The sequence of the polypeptide of SEQ ID NO: 2 can thus be modified to provide polypeptides of the invention. Amino acid substitutions may be made, for example, 1, 2, 3 or 4 substitutions. The modified polypeptide retains activity as an alpha amylase.

In an aspect the polypeptide of the invention has at least 99.5% identity to a polypeptide having an amino acid sequence as set out in SEQ ID NO: 2 or having an amino acid sequence as set out in amino acids 34 to 719 of SEQ ID NO: 2.

Preferably, such an polypeptide has an amino acid sequence which, when aligned with the amino acid sequence as set in SEQ ID NO 2, comprises at least one of Asp at position 184, Ala at position 297, Thr at position 368 and Asn at position 489, said positions being defined with reference to SEQ ID NO: 2. Preferably such an alpha-amylase comprises at least Ala at position 297 said position being defined with reference to SEQ ID NO: 2.

In an aspect the polypeptide of the invention may comprise at least two of Asp at position 184, Ala at position 297, Thr at position 368 and Asn at position 489, said positions being defined with reference to SEQ ID NO: 2. Preferably such a polypeptide comprises at least: Asp at position 184 and Ala at position 297; at least Ala at position 297 and Thr at position 368; or at least Ala at position 297 and Asn at position 489, all of said positions being defined with reference to SEQ ID NO: 2.

In an aspect the polypeptide of the invention may comprise at least three of Asp at position 184, Ala at position 297, Thr at position 368 and Asn at position 489, said positions being defined with reference to SEQ ID NO: 2. Preferably, such a polypeptide comprises at least: Ala at position 297, Thr at position 368 and Asn at position 489; Asp at position 184, Ala at position 297 and Thr at position 368; or Asp at position 184, Ala at position 297 and Asn at position 489, all of said positions being defined with reference to SEQ ID NO: 2.

In an aspect the polypeptide of the invention may comprise Asp at position 184, Ala at position 297, Thr at position 368 and Asn at position 489, all of said positions being defined with reference to SEQ ID NO: 2.

The one or more amino acids of the polypeptide according to the invention may be substituted in order to improve the expression in a host cell. In addition one or more amino acids of the protein according to the invention may be substituted to change the enzymes specific activity or thermal stability.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine.

Preferred conservative amino acids substitution groups include: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids include: Ala to ser; Arg to lys; Asn to gln or his; Asp to glu; Cys to ser or ala; Gln to asn; Glu to asp; Gly to pro; His to asn or gin; He to leu or val; Leu to ile or val; Lys to arg; gin or glu; Met to leu or ile; Phe to met, leu or tyr; Ser to thr; Thr to ser; Trp to tyr; Tyr to trp or phe; and, Val to ile or leu.

Polypeptides of the invention may be in a substantially isolated form. It will be understood that the polypeptide may be mixed with carriers or diluents which will not interfere with the intended purpose of the polypeptide and still be regarded as substantially isolated. The polypeptide of the invention may also be in a substantially purified form, in which case it will generally comprise the polypeptide in a preparation in which more than 50%. e.g. more than 80%, 90%, 95% or 99%, by weight of the polypeptide in the preparation is a polypeptide of the invention.

For example, recombinantly produced polypeptides and proteins produced in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The polypeptide of the invention may be chemically modified, e.g. post-translationally modified. For example, they may be glycosylated or comprise modified amino acid residues. They may also be modified by the addition of Histidine residues or a T7 tag to assist their purification or by the addition of a signal sequence to promote their secretion from a cell. Such modified polypeptides and proteins fall within the scope of the term "polypeptide" of the invention.

For secretion of the translated protein into the lumen of the endoplasmic reticulum, into the periplasmic space or into the extracellular environment, an appropriate secretion signal sequence may be fused to the polynucleotide of the invention. The signals may be endogenous to the polypeptide or they may be heterologous signals.

The polypeptide according to the invention may be produced in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Sequence Identity

The terms "homology", "percent identity", "percent homology" and "percentage of identity" are used interchangeably herein. For the purpose of this invention, it is defined here that in order to determine the percent homology of two amino acid sequences or of two polynucleotide sequences (also referred to herein as nucleic acid sequences), the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The percent homology or percent identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and polynucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277. For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of identity between a query sequence and a sequence of the invention is calculated as follows: Number of corresponding positions in the alignment showing an identical aminoacid or identical nucleotide in both sequences divided by the total length of the alignment after substraction of the total number of gaps in the alignment. The percent identity defined as herein can be obtained from NEEDLE by using the NOBRIEF option and is labelled in the output of the program as "longest-identity".

The polynucleotide and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the polynucleotide of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information.

Vectors

Polynucleotides of the invention can be incorporated into a vector, including cloning and expression vectors. A vector may be a recombinant replicable vector. The vector may be used to replicate a polynucleotide of the invention in a compatible host cell. The vector may conveniently be subjected to recombinant DNA procedures The invention also pertains to methods of growing, transforming or transfecting such vectors in a suitable host cell, for example under conditions in which expression of a polypeptide of the invention occurs. The invention provides a method of making polypeptides of the invention by introducing a polynucleotide of the invention into a vector, in an embodiment an expression vector, introducing the vector into a compatible host cell, and growing the host cell under conditions which bring about replication of the vector. The vector may be recovered from the host cell.

A vector according to the invention may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

One type of vector is a "plasmid", which refers to a circular double stranded DNA loop into which additional DNA segments can be inserted. Another type of vector is a viral vector, wherein additional DNA segments can be inserted into the viral genome. Certain vectors are capable of autonomous replication in a host cell into which they are introduced (e.g., bacterial vectors having a bacterial origin of replication and episomal mammalian vectors). Other vectors (e.g., bacterial integration vector with out a suitable origin of replication or a non-episomal mammalian vectors) are integrated into the genome of a host cell upon introduction into the host cell, and thereby are replicated along with the host genome.

Moreover, certain vectors are capable of directing the expression of genes to which they are operatively linked. Such vectors are referred to herein as "expression vectors". The terms "expression vector", "expression construct" and "recombinant expression vector" are used interchangeably herein. In general, expression vectors of utility in recombinant DNA techniques are often in the form of plasmids. The terms "plasmid" and "vector can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell, for example a bacterial cell, and used for the production of an alpha-amylase as encoded by a polynucleotide of the invention.

The recombinant expression vectors of the invention comprise a polynucleotide of the invention in a form suitable for expression of the polynucleotide in a host cell, which means that the recombinant expression vector includes one or more regulatory sequences, selected on the basis of the host cells to be used for expression, which is operably linked to the polynucleotide sequence to be expressed.

Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under conditions compatible with the control sequences or the sequences are arranged so that they function in concert for their intended purpose, for example transcription initiates at a promoter and proceeds through the DNA sequence encoding the polypeptide.

The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990).

The term regulatory sequences includes those sequences which direct constitutive expression of a nucleotide sequence in many types of host cells and those which direct expression of the nucleotide sequence only in a certain host cell (e.g. tissue-specific regulatory sequences).

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; (2) a ribosome binding site to facilitate the translation of the transcribed RNA (3) optionally, a signal sequence capable of directing secretion of the polypeptide from the given host cell into a culture medium; (4) a polynucleotide sequence according to the invention; and preferably also (5) a transcription termination region (terminator) capable of terminating transcription downstream of the nucleotide sequence encoding the polypeptide.

Downstream of the nucleotide sequence according to the invention there may be a 3' untranslated region containing one or more transcription termination sites (e.g. a terminator, herein also referred to as a stop codon). The origin of the terminator is less critical. The terminator can, for example, be native to the DNA sequence encoding the polypeptide. However, preferably a bacterial terminator is used in bacterial host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a start codon is usually AUG (or ATG), but there are also alternative start codons, such as for example GUG (or GTG) and UUG (or TTG), which are used in prokaryotes. Also a stop or translation termination codon is appropriately positioned at the end of the polypeptide to be translated.

Enhanced expression of the polynucleotide of the invention may also be achieved by the selection of homologous and heterologous regulatory regions, e.g. promoter, secretion leader and/or terminator regions, which may serve to increase expression and, if desired, secretion levels of the protein of interest from the expression host and/or to provide for the inducible control of the expression of a polypeptide of the invention.

It will be appreciated by those skilled in the art that the design of the expression vector can depend on such factors as the choice of the host cell to be transformed, the level of expression of protein desired. The expression vectors of the invention can be introduced into host cells to thereby produce proteins or peptides, encoded by polynucleotides as described herein (e.g. the polypeptide having alpha amylase activity according to the invention or a variant thereof as described herein).

The recombinant expression vectors of the invention, also referred to herein as "vector of the invention" can be designed for expression of the polypeptides according to the invention in prokaryotic or eukaryotic cells. For example, the polypeptides according to the invention can be produced in bacterial cells such as *E. coli* and Bacilli, insect cells (using baculovirus expression vectors), fungal cells, yeast cells or mammalian cells. Suitable host cells are discussed herein and further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

For most bacteria, filamentous fungi and yeasts, the vector or expression construct is preferably integrated in the genome of the host cell in order to obtain stable transformants. In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors which is a plasmid, bacteriophage, yeast episome, yeast chromosomal elements, viruses such as baculoviruses, papova viruses, vaccinia viruses, adenoviruses, fowl pox viruses, pseudorabies viruses and retroviruses, and vectors which are combinations thereof, such as those consisting of plasmid and bacteriophage genetic elements, such as cosmids and phagemids.

The polynucleotide according to the invention should be operatively linked to an appropriate promoter. Aside from the promoter native to the gene encoding the polypeptide of the invention, other promoters may be used to direct expression of the polypeptide of the invention. The promoter may be selected for its efficiency in directing the expression of the polypeptide of the invention in the desired expression host. A suitable promoter may be one which is an "inducible promoter" is one which causes mRNA synthesis of a gene to be initiated temporally under specific conditions. Alternatively, a promoter may be a "constitutive" promoter, i.e. one that permits the gene to be expressed under virtually all environmental conditions, i.e. a promoter that directs constant, non-specific gene expression. A "strong constitutive promoter", i.e., a promoter which causes mRNAs to be initiated at high frequency compared to a native host cell may be used.

In the invention, bacteria may preferably be used as host cells for the expression of a polypeptide of the invention, in particular Bacilli. Suitable inducible promoters useful in such host cells include; (i) Promoters may be regulated primarily by an ancillary factor such as a repressor or an activator. The repressors are sequence-specific DNA binding proteins that repress promoter activity. The transcription can be initiated from this promoter in the presence of an inducer that prevents binding of the repressor to the operator of the promoter. Examples of such promoters from Gram-positive microorganisms include, but are not limited to, gnt (gluconate operon promoter); penP from *Bacillus licheniformis*; glnA (glutamine synthetase); xylAB (xylose operon); araABD (L-arabinose operon) and $P_{spac}$ promoter, a hybrid SPO1/lac promoter that can be controlled by inducers such as isopropyl-β-D-thiogalactopyranoside [IPTG] ((Yansura D. G., Henner D. J. Proc Natl Acad Sci USA. 1984 81(2):439-443). Activators are also sequence-specific DNA binding proteins that induce promoter activity. Examples of such promoters from Gram-positive microorganisms include, but are not limited to, two-component systems (PhoP-PhoR, DegU-DegS, Spo0A-Phosphorelay), LevR, Mry and GltC. (ii) Production of secondary sigma factors can be primarily responsible for the transcription from specific promoters. Examples from Gram-positive microorganisms include, but are not limited to, the promoters activated by sporulation specific sigma factors: $\sigma^F$, $\sigma^E$, $\sigma^G$ and $\sigma^K$ and general stress sigma factor, $\sigma^B$. The $\sigma^B$-mediated response is induced by energy limitation and environmental stresses (Hecker M, Völker U. Mol Microbiol. 1998; 29(5): 1129-1136.). (iii) Attenuation and antitermination also regulates transcription. Examples from Gram-positive microorganisms include, but are not limited to, trp operon and sacB gene. (iv) Other regulated promoters in expression vectors are based the sacR regulatory system conferring sucrose inducibility (Klier A F, Rapoport G. Annu Rev Microbiol. 1988:42:65-95).

Strong constitutive promoters are well known and an appropriate one may be selected according to the specific sequence to be controlled in the host cell. Suitable inducible promoters useful in bacteria, such as Bacilli, include: promoters from Gram-positive microorganisms such as, but are not limited to, SP01-26, SP01-15, veg, pyc (pyruvate carboxylase promoter), and amyE. Examples of promoters from Gram-negative microorganisms include, but are not limited to, tac, tet, trp-tet, lpp, lac, lpp-lac, laclq, T7, T5, T3, gal, trc, ara, SP6, $\lambda$-$P_R$, and $\lambda$-$P_L$.

Additional examples of promoters useful in bacterial cells, such as Bacilli, include the $\alpha$-amylase and SPo2 promoters as well as promoters from extracellular protease genes.

In an embodiment, the promoter sequences may be obtained from a bacterial source. In another embodiment, the promoter sequences may be obtained from a gram positive bacterium such as a *Bacillus* strain, e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

An example of a suitable promoter for directing the transcription of a polynucleotide sequence in the methods of the present invention is the promoter obtained from the *E. coli* lac operon. Another example is the promoter of the *Streptomyces coelicolor* agarase gene (dagA). Another example is the promoter of the *Bacillus lentus* alkaline protease gene (aprH). Another example is the promoter of the *Bacillus licheniformis* alkaline protease gene (subtilisin Carlsberg gene). Another example is the promoter of the *Bacillus subtilis* levansucrase gene (sacB). Another example is the promoter of the *Bacillus subtilis* alphaamylase gene (amyF). Another example is the promoter of the *Bacillus licheniformis* alphaamylase gene (amyL). Another example is the promoter of the *Bacillus stearothermophilus* maltogenic amylase gene (amyM). Another example is the promoter of the *Bacillus amyloliquefaciens* alpha-amylase gene (amyQ). Another example is a "consensus" promoter having the sequence TTGACA for the "−35" region and TATAAT for the "−10" region. Another example is the promoter of the *Bacillus licheniformis* penicillinase gene (penP). Another example are the promoters of the *Bacillus subtilis* xylA and xylB genes.

A variety of promoters can be used that are capable of directing transcription in the recombinant host cells of the invention. Preferably the promoter sequence is from a highly expressed gene. Examples of preferred highly expressed genes from which promoters may be seleleted and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK or PKI), alcohol dehydrogenases (ADH), as well as genes encoding amylases, glucoamylases, proteases, xylanases, cellobiohydrolases, $\beta$-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which may be used in fungal expression host cells include those which are obtainable from the fungal genes for xylanase (x/nA), phytase, ATP-synthetase, subunit 9 (oliC), triose phosphate isomerase (tpi), alcohol dehydrogenase (AdhA), a-amylase (amy), amyloglucosidase (AG-from the glaA gene), acetamidase (amdS) and glyceraldehyde-3-phosphate dehydrogenase (gpd) promoters.

All of the above-mentioned promoters are readily available in the art.

The vector may contain a polynucleotide of the invention oriented in an antisense direction to provide for the production of antisense RNA.

Vector DNA can be introduced into prokaryotic or eukaryotic cells via natural competence, conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation. DEAE-dextran-mediated transfection, transduction, infection, lipofection, cationic lipidmediated transfection or electroporation. Suitable methods for transforming or transfecting host cells can be found in Sambrook, et al. (supra) and other laboratory manuals.

In order to identify and select cells which harbour a vector, a gene that encodes a selectable marker (e.g., resistance to antibiotics) is generally introduced into the host cells along with the polynucleotide of the invention. Preferred selectable markers include, hut are not limited to, those which confer resistance to drugs or which complement a defect in the host cell.

Such markers include ATP synthetase, subunit 9 (oliC), orotidine-5'-phosphatedecarboxylase (pvrA), the bacterial G418 resistance gene (this may also be used in yeast, but not in fungi), the ampicillin resistance gene (*E. coli*), resistance genes for, neomycin, kanamycin, tetracycline, spectinomycin, erythromycin, chloramphenicol, phleomycin (*Bacillus*) and the *E. coli* uidA gene, coding for $\beta$-glucuronidase (GUS). Vectors may be used in vitro, for example for the production of RNA or used to transfect or transform a host cell.

They also include e.g. versatile marker genes that can be used for transformation of most filamentous fungi and yeasts such as acetamidase genes or cDNAs (the amdS, niaD, facA genes or cDNAs from *A. nidulans, A. oryzae* or *A. niger*), or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e.g. D-alanine racemase (from *Bacillus*), URA3 (from *S. cerevisiae* or analogous genes from other yeasts), pyrG or pyrA (from *A. nidulans* or *A. niger*), argB (from *A. nidulans* or *A. niger*) or trpC. In an embodiment the selection marker is deleted from the transformed host cell after introduction of the expression construct so as to obtain transformed host cells capable of producing the polypeptide which are free of selection marker genes.

Expression of proteins in prokaryotes is often carried out in with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Vectors of the invention may be transformed into a suitable host cell as described herein to provide for expression of a polypeptide of the invention. Thus, in a further aspect the invention provides a process for preparing a polypeptide according to the invention which comprises cultivating a host cell transformed or transfected with an expression vector encoding the polypeptide, and recovering the expressed polypeptide.

Host Cells

The invention further provides "recombinant host cells" also referred herein as "host cells" transformed or transfected with the vectors for the replication and/or expression of polynucleotides of the invention. The cells will be chosen to be compatible with the said vector. Promoters and other expression regulation signals may be selected to be compatible with the host cell for which expression is designed.

The invention features cells, e.g., transformed host cells or recombinant host cells comprising a polynucleotide according to the invention or comprising a vector according to the invention.

A "transformed host cell" or "recombinant host cell" is a cell into which (or into an ancestor of which) has been introduced, by means of recombinant DNA techniques, a polynucleotide according to the invention. Both prokaryotic and eukaryotic cells are included, e.g., bacteria, fungi, yeast, insect, mammalian and the like.

Preferred are cells of a *Bacillus* strain, e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

According to another aspect, the host cell is a eukaryotic host cell. Preferably, the eukaryotic cell is a mammalian, insect, plant, fungal, or algal cell. Preferred mammalian cells include e.g. Chinese hamster ovary (CHO) cells, COS cells, 293 cells, PER.C6® fetal cell line cells, and hybridomas. A number of vectors suitable for stable transfection of mammalian cells are available to the public, methods for constructing such cell lines are also publicly known, e.g., in Ausubel et al. (supra).

In an embodiment insect cells include e.g. Sf9 and Sf21 cells and derivatives thereof.

In an embodiment the eukaryotic cell is a fungal cell, i.e. a yeast cell, such as *Candida, Hansenula, Kluyveromyces, Pichia, Saccharomyces, Schizosaccharomyces*, or *Yarrowia* strain. Preferably from *Kluyveromyces lactis, S. cerevisiae, Hansenula polymorpha, Yarrowia lipolytica* and *Pichia pastoris*, or a filamentous fungal cell.

Filamentous fungi include all filamentous forms of the subdivision *Eumycota* and *Oomycota* (as defined by Hawksworth at al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium*, and *Trichoderma*. In an embodiment filamentous fungal cells belong to a species of an *Aspergillus, Chrysosporium, Penicillium, Talaromyces, Fusarium* or *Trichoderma* genus, and preferably a species of *Aspergillus niger, Aspergillus awamori, Aspergillus foetidus, Aspergillus sojae, Aspergillus fumigatus, Talaromyces emersonii, Aspergillus oryzae, Chrysosporium lucknowense, Myceliophthora thermophila, Fusarium oxysporum, Trichoderma reesei* or *Penicillium chrysogenum*. In an embodiment the host cell is *Aspergillus niger*.

If the host cell according to the invention is an *Aspergillus niger* host cell, the host cell preferably is CBS 513.88, CBS124.903 or a derivative thereof.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein produced. To this end, eukaryotic host cells that possess the cellular machinery for proper processing of the primary transcript, glycosylation, and phosphorylation of the gene product can be used. Such host cells are well known in the art.

If desired, a host cell as described above may be used to in the preparation of a polypeptide according to the invention. Such a method typically comprises cultivating a recombinant host cell (e.g. transformed or transfected with an expression vector as described above) under conditions to provide for expression (by the vector) of a coding sequence encoding the polypeptide, and optionally recovering, more preferably recovering and purifying the produced polypeptide from the cell or culture medium. Polynucleotides of the invention can be incorporated into a recombinant replicable vector, e.g. an expression vector. The vector may be used to replicate the polynucleotide in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably the polypeptide according to the invention is produced as a secreted protein in which case the nucleotide sequence encoding a mature form of the polypeptide in the expression construct is operably linked to a nucleotide sequence encoding a signal sequence. Preferably the signal sequence is native (homologous), also referred to herein as "wild type" to the nucleotide sequence encoding the polypeptide. Alternatively the signal sequence is foreign (heterologous) to the nucleotide sequence encoding the polypeptide, in which case the signal sequence is preferably endogenous to the host cell in which the nucleotide sequence according to the invention is expressed. Examples of suitable signal sequences for Bacilli are from the amyE, yurl fliL, vpr, glpQ, play, lytC, ywsB, ybbD, ybxl, yolk, ylqB, ybbC, pel, yckD, ywaD, ywmD, yweA, yraJ, dacF, yfjS, yybN, yrpD, yvcE, wprA, yxaL, ykwD, yncM2, sacB, phrC, SacC, yoqM, ykoJ, lip, yfkN, yurI, ybfO, yfkD, yoaJ, xynA, penP, ydjM, yddT, yojL, yomL, yqxI, yrvJ, yvpA, yjcM, yjfA, ypjP, ggt, yoqH, ywtD, ylaE, yraJ, lytB, lytD, nprB, nucB, rplR, yfhK, yjdB, ykvV, ybbE, yuiC, ylbL, yacD, yvpB genes from *Bacillus subtilis*. Suitable yeast signal sequences are those from yeast a-factor genes. Similarly, a suitable signal sequence for filamentous fungal host cells is e.g. a signal sequence those from a filamentous fungal amyloglucosidase (AG) gene, e.g. the *A. niger* glaA gene. This may be used in combination with the amyloglucosidase (also called (gluco) amylase) promoter itself, as well as in combination with other promoters. Hybrid signal sequences may also be used with the context of the present invention.

Preferred heterologous secretion leader sequences are those originating from the fungal amyloglucosidase (AG) gene (glaA-both 18 and 24 amino acid versions e.g. from *Aspergillus*), the α-factor gene (yeasts e.g. *Saccharomyces* and *Kluyveromyces*) or the α-amylase (amyE, amyQ and amyL) and alkaline protease aprE and neutral protease genes (*Bacillus*). The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

The invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

A heterologous host cell may also be chosen wherein the polypeptide of the invention is produced in a form which is substantially free of enzymatic activities that might interfere with the applications, e.g. free from starch degrading, cellulose-degrading or hemicellulose degrading enzymes. This may be achieved by choosing a host cell which does not normally produce such enzymes.

The invention encompasses processes for the production of the polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is a host cell which is of the same species or which is a variant within the same species as the species from which the DNA sequence is obtained.

The host cell may over-express the polypeptide, and techniques for engineering over-expression are well known. The host may thus have two or more copies of the encoding polynucleotide (and the vector may thus have two or more copies accordingly).

Therefore in one embodiment of the invention the recombinant host cell according to the invention is capable of expressing or overexpressing a polynucleotide or vector according to the invention.

Another aspect of the invention is a method for producing a polypeptide of the invention comprising (a) culturing a recombinant host cell according to the invention under conditions such that the polypeptide of the invention is produced; and (b) optionally recovering the polypeptide of the invention from the cell culture medium.

According to the present invention, the production of the polypeptide of the invention can be effected by the culturing of a host cell according to the invention, which has been transformed with one or more polynucleotides of the present invention, in a conventional nutrient fermentation medium. The method of the invention comprises the step of culturing a host cell of the invention under conditions such that a polypeptide of the invention is produced.

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culture is stopped and the polypeptide is recovered using known procedures.

The term "culturing" includes maintaining and/or growing a living recombinant host cell of the present invention, in particular the recombinant host cell according to the invention. In one aspect, a recombinant host cell of the invention is cultured in liquid media. In another aspect, a recombinant host cell is cultured in solid media or semi-solid media.

Preferably, the recombinant host cell of the invention is cultured in liquid media comprising nutrients essential or beneficial to the maintenance and/or growth of the recombinant host cell. Such nutrients include, but are not limited to, carbon sources or carbon substrates, e.g. complex carbohydrates such as bean or grain meal, starches, sugars, sugar alcohols, hydrocarbons, oils, fats, fatty acids, organic acids and alcohols; nitrogen sources, e.g. vegetable proteins, peptones, peptides and amino acids obtained from grains, beans and tubers, proteins, peptides and amino acids obtained from animal sources such as meat, milk and animal byproducts such as peptones, meat extracts and casein hydrolysates; inorganic nitrogen sources such as urea, ammonium sulfate, ammonium chloride, ammonium nitrate and ammonium phosphate; phosphorous sources, e.g. phosphoric acid, sodium and potassium salts thereof; trace elements, e.g. magnesium, iron, manganese, calcium, copper, zinc, boron, molybdenum and/or cobalt salts; as well as growth factors such as amino acids, vitamins, growth promoters and the like.

The selection of the appropriate medium may be based on the choice of expression host, i.e. the choice of the recombinant host cell and/or based on the regulatory requirements of the expression construct. Such media are known to those skilled in the art. The medium may, if desired, contain additional components favouring the transformed expression hosts over other potentially contaminating microorganisms.

The recombinant host cells may be cultured in liquid media either continuously or intermittently, by conventional culturing methods such as standing culture, test tube culture, shaking culture, aeration spinner culture or fermentation. Preferably, the recombinant host cells are cultured in a fermentor. Fermentation processes of the invention include batch, fed-batch and continuous methods of fermentation. A variety of such processes have been developed and are well known in the art.

The recombinant host cells are preferably cultured under controlled pH. In one embodiment, recombinant host cells may be cultured at a pH of between 4.5 and 8.5, preferably 6.0 and 8.5, more preferably at a pH of about 7. The desired pH may be maintained by any method known to those skilled in the art.

Preferably, the recombinant host cells are further cultured under controlled aeration and under controlled temperatures. In one embodiment, the controlled temperatures include temperatures between 15 and 70° C., preferably the temperatures are between 20 and 55° C., more preferably between 30 and 50° C.

The appropriate conditions are usually selected based on the choice of the expression host and the protein to be produced.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means, including, but not limited to, treatment with a conventional resin, treatment with a conventional adsorbent, alteration of pH, solvent extraction, dialysis, filtration, concentration, crystallization, recrystallization, pH adjustment, lyophilisation and the like.

For example, the alpha-amylase enzyme according to the invention can be recovered and purified from recombinant cell cultures by methods known in the art (Protein Purification Protocols, Methods in Molecular Biology series by Paul Cutler, Humana Press, 2004).

Usually, the compound is "isolated" when the resulting preparation is substantially free of other components. In one embodiment, the preparation has a purity of greater than about 80% (by dry weight) of the desired compound (e.g. less than about 20% of all the media, components or fermentation byproducts), in another embodiment greater than about 90% of the desired compound, in another embodiment greater than about 95% of the desired compound and in another embodiment greater than about 98 to 99% of the desired compound.

Alternatively, however, the desired compound is not purified from the recombinant host cell or the culture. The entire culture or the culture supernatant may be used as a source of the product. In a specific embodiment, the culture or the culture supernatant is used without modification. In a further embodiment, the culture or the culture supernatant is concentrated, dried and/or lyophilized.

The recombinant host cell of the invention is capable of producing a polypeptide of the invention compound under suitable conditions. Preferably, production of a polypeptide of the invention means production of at least about 50 mg, about 100 mg, about 200 mg, about 500 mg, about 1 g, about 3 g, about 5 g or about 10 g polypeptide of the invention per liter culture medium, Enzyme Preparation

*Bacillus* strain DSM-AMB154-1 (see examples) was cultivated under aerobic conditions in a suitable fermentation medium.

A suitable medium medium may contain assimilable sources of carbon and nitrogen besides inorganic salts optionally together with growth promoting nutrients, such as yeast extract. Fermentation is typically conducted at 35-40° C. and at a pH of 6.5-7.5 and preferably kept approximately constant by automatic means. The enzyme is excreted into the medium. At the end of fermentation, if required, the production host may be killed by means known by the person skilled in the art. The ensuing fermentation broth may be freed of bacterial cells, debris therefrom together with other solids, for example by filtration or centrifugation. The filtrate or supernatant containing the enzyme may be further clarified, for example by filtration or centrifugation, and then concentrated as required, for example by ultrafiltration or in an evaporator under reduced pressure to give a concentrate which, if desired, may be taken to dryness, for example by lyophilization or spray-drying. Typically, the resulting crude enzyme product exhibits an activity in the range of about 10,000-500,000 MU per gram.

The polynucleotide according to the invention comprises a nucleotide sequence selected from:

The invention relates to a polynucleotide encoding for a polypeptide having alpha-amylase activity comprising:
  (a) a polynucleotide sequence encoding a polypeptide having an amino acid sequence as set out in SEQ ID NO: 2 or having an amino acid sequence as set out in amino acids 34 to 719 of SEQ ID NO: 2; or
  (b) a polynucleotide sequence encoding a polypeptide having at least 99.5% identity to a polypeptide having an amino acid sequence as set out in amino acids 34 to 719 of SEQ ID NO: 2; or
  (c) a polynucleotide sequence as set out in nucleotides 100 to 2157 of SEQ ID NO: 1 or SEQ ID NO: 3; or
  (d) a polynucleotide sequence as set out SEQ ID NO: 1 or SEQ ID NO: 3.

The polynucleotide according to the invention encodes for an alpha-amylase.

In an embodiment of the polynucleotide according to the invention, the polynucleotide is an isolated polynucleotide comprising:
  (a) a polynucleotide sequence as set out in SEQ ID NO: 1 or 3; or
  (b) a polynucleotide sequence as set out in nucleotides 100 to 2157 of the polynucleotide sequence of SEQ ID NO: 1 or 3 (inclusive of nucleotides 100 and 2157, for the avoidance of doubt); or
  (c) a polynucleotide sequence encoding a polypeptide having an amino acid sequence as set out in SEQ ID NO: 2 or having an amino acid sequence as set out in amino acids 34 to 719 of SEQ ID NO: 2 (inclusive of amino acids 34 and 719, for the avoidance of doubt).

In an embodiment of the polynucleotide according to the invention, the polynucleotide is produced by *Alicyclobacillus pohliae* NCIMB14276.

In a further aspect of the polynucleotide according to the invention the isolated polynucleotide is produced by *Alicyclobacillus pohliae* NCIMB14276.

The vector according to the invention comprises the polynucleotide sequence according to the invention.

In an embodiment of the vector according to the invention the vector is an expression vector, wherein the polynucleotide sequence according to the invention is operably linked with at least one regulatory sequence allowing for expression of the polynucleotide sequence in a suitable host cell.

Suitable host cells include bacteria, including *Escherichia, Anabaena, Caulobactert, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. In an aspect of the vector according to the invention, the host cell is a the bacterial cell is selected from the group consisting of *B. subtilis, B. puntis, B. megaterium, B. halodurans, B. pumilus, G. oxydans, Caulobactert crescentus* CB 15, *Methylobacterium extorquens, Rhodobacter sphaeroides, Pseudomonas zeaxanthinifaciens, Paracoccus denitrificans, C. glutamicum, Staphylococcus carnosus, Streptomyces lividans, Sinorhizobium melioti* and *Rhizobium radiobacter*.

In a further embodiment of the vector according to the invention the suitable host cell is a is an *Aspergillus, Bacillus, Chrysosporium, Escherichia, Kluyveromyces, Penicillium, Pseudomonas, Saccharomyces, Streptomyces* or *Talaromyces* species, preferably the host cell is a *Bacillus subtilis, Bacillus*

*amyloliquefaciens, Bacillus licheniformis, Escherichia coli, Aspergillus Niger* or *Aspergillus oryzae* species.

The recombinant host cell according to the invention may comprise the polynucleotide according to the invention or the vector according to the invention.

In an embodiment of the recombinant host cell according the invention, the recombinant host cell is capable of expressing or over-expressing the polynucleotide according to the invention or the vector according to the invention.

The method according to the invention for manufacturing the polynucleotide according to the invention or the vector according to the invention comprises the steps of culturing a host cell transformed with said polynucleotide or said vector and isolating said polynucleotide or said vector from said host cell.

The polypeptide according to the invention comprises:
an alpha-amylase polypeptide comprising:
(a) an amino acid sequence as set out in amino acids 34 to 9 of SEQ ID NO: 2; or
(b) an amino acid sequence having at least 99.5% identity to an amino acid sequence as set out in amino acids 34 to 719 of SEQ ID NO: 2; or
(c) an amino acid sequence encoded by a polynucleotide as set out in nucleotides 100 to 2157 of SEQ ID NO: 1 or SEQ ID NO: 3.

In an embodiment of the polypeptide according to the invention, the polypeptide is an isolated polypeptide comprising:
(a) amino acid sequence as set out in amino acids 34 to 719 of SEQ ID NO: 2; or
(b) an amino acid sequence encoded by the polynucleotide as set out in nucleotides 100 to 2157 of SEQ ID NO: 1 or 3; or
(c) the amino acid sequence according to (b), wherein the polynucleotide is produced by *Alicyclobacillus pohliae* NCIMB14276.

In an embodiment of the polypeptide according to the invention, the polypeptide is obtainable by expressing the polynucleotide according to the invention or the vector according to the invention in an appropriate host cell.

The method according to the invention for manufacturing the polypeptide according the invention comprises cultivating the recombinant host cell according to the invention under condition which allow for expression of the polynucleotide according to the invention or the vector according to the invention and, optionally, recovering the encoded polypeptide from the cell or culture medium.

In an embodiment of the method according to the invention for manufacturing the polypeptide according to the invention the method comprises cultivating a host cell comprising a vector, the vector comprising a polynucleotide comprising:
(a) a polynucleotide sequence as set out in SEQ ID NO: 1 or 3; or
(b) a polynucleotide sequence as set out in nucleotides 100 to 2157 of the polynucleotide sequence of SEQ ID NO: 1 or 3 (inclusive of nucleotides 100 and 2157, for the avoidance of doubt); or
(c) a polynucleotide sequence encoding a polypeptide having an amino acid sequence as set out in SEQ ID NO: 2 or having an amino acid sequence as set out in amino acids 34 to 719 of SEQ ID NO: 2 (inclusive of amino acids 34 and 719, for the avoidance of doubt),
under conditions which allow for expression of the vector and, optionally, recovering the encoded polypeptide from the cell or culture medium.

In an embodiment of the method according to the invention for manufacturing the polypeptide according to the invention the method comprises cultivating a host cell comprising a polynucleotide, said polynucleotide comprising:
(a) a polynucleotide sequence as set out in SEQ ID NO: 1 or 3; or
(b) a polynucleotide sequence as set out in nucleotides 100 to 2157 of the polynucleotide sequence of SEQ ID NO: 1 or 3 (inclusive of nucleotides 100 and 2157, for the avoidance of doubt); or
(c) a polynucleotide sequence encoding a polypeptide having an amino acid sequence as set out in SEQ ID NO: 2 or having an amino acid sequence as set out in amino acids 34 to 719 of SEQ ID NO: 2 (Inclusive of amino acids 34 and 719, for the avoidance of doubt),
under conditions which allow for expression of the polynucleotide and,
optionally, recovering the encoded polypeptide from the cell or culture medium.

The polypeptide according to the invention may be used in food manufacturing.

In an embodiment of the use in food manufacturing, the use is the manufacture of a baked product, including without limitation a bread or a cake.

The enzyme composition according to the invention comprises the polypeptide according to the invention and one or more components selected from the group consisting of milk powder, gluten, granulated fat, an additional enzyme, an amino acid, a salt, oxidants (including ascorbic acid, bromate and Azodicarbonamide (ADA)), reducing agents (including L-cysteine), emulsifiers (including mono/di glycerides such as glycerol monostearate (GMS), sodium stearoyl lactylate (SSL), calcium stearoyl lactylate (CSL), polyglycerol esters of fatty acids (PGE) and DATEM), gums (including guargum and xanthangum), flavours, acids (including citric acid, propionic acid), starch, modified starch, gluten, humectants (including glycerol) and preservatives.

In an embodiment of the enzyme composition according to the invention the additional enzyme is a lipolytic enzyme, preferably a phospholipase, a galactolipase or an enzyme having both phospholipase and galactolipase activity.

In an embodiment of the enzyme composition according to the invention the additional enzyme is a phospholipase.

In an embodiment of the enzyme composition according to the invention the additional enzyme is a galactolipase.

In an embodiment of the enzyme composition according to the invention the additional enzyme is an enzyme having both phospholipase and galactolipase activity.

The method according to the invention to prepare a dough comprises the step of combining the polypeptide according to the invention or the enzyme composition according to the invention and at least one dough ingredient. 'Combining' includes without limitation, adding the polypeptide or the enzyme composition according to the invention to the at least one dough ingredient, adding the at least one dough ingredient to the polypeptide or the enzyme composition according to the invention, mixing the polypeptide according to the invention and the at least one dough ingredient.

In an aspect of the method according to the invention to prepare a dough, the method comprises the steps of combining the polypeptide according to the invention and at least one component selected from flour, egg, water, salt, sugar, flavours, fat (including butter, margarine, oil and shortening), baker's yeast, a chemical leavening systems, milk, oxidants (including ascorbic acid, bromate and Azodicarbonamide (ADA)), reducing agents (including L-cysteine), emulsifiers (including mono/di glycerides such as glycerol monostearate (GMS), sodium stearoyl lactylate (SSL) is the calcium stearoyl lactylate (CSL) is polyglycerol esters of fatty acids (PGE) and DATEM), gums (including guargum and xanthangum), acids (including citric acid, propionic acid), starch, modified starch, gluten, humectants (including glycerol) and preservatives.

In an aspect of the method according to the invention to prepare a dough, the method comprises the steps of combining the enzyme composition according to the invention and at least one component selected from flour, egg, water, salt, sugar, flavours, fat (including butter, margarine, oil and shortening), baker's yeast, a chemical leavening systems, milk, oxidants (including ascorbic acid, bromate and Azodicarbonamide (ADA)), reducing agents (including L-cysteine), emulsifiers (including mono/di glycerides such as glycerol monostearate (GMS), sodium stearoyl lactylate (SSL), calcium stearoyl lactylate (CSL), polyglycerol esters of fatty acids (PGE) and DATEM), gums (including guargum and xanthangum), acids (including citric acid, propionic acid), starch, modified starch, gluten, humectants (including glycerol) and preservatives.

'Combining' in the above two aspects includes without limitation, adding the polypeptide or the enzyme composition according to the invention to the at least one component indicated above, adding the at least one component indicated above to the polypeptide or the enzyme composition according to the invention, mixing the polypeptide according to the invention and the at least one component indicated above.

A dough according to the invention may comprise the polypeptide according to the invention or the enzyme composition according to the invention.

The method according to the invention to prepare a baked product comprises the step of baking the dough according to the invention.

In an embodiment of the method to prepare a baked product, the method comprises baking a dough comprising the polypeptide according to the invention.

In an embodiment of the method to prepare a baked product, the method comprises baking a dough comprising the enzyme composition according to the invention.

In an embodiment of the method to prepare a baked product the baked product is bread or cake.

The baked product according to the invention is obtainable by the method according to the invention to prepare the baked product.

The method according the invention to produce a polypeptide having at least 60% identity, in an embodiment at least 70% identity, in an embodiment at least 80% identity, in an embodiment at least 85% identity, in an embodiment at least 90% identity, in an embodiment at least 95% identity with
(a) a polypeptide having an amino acid sequence as set out in amino acids 34 to 719 of SEQ ID NO: 2; or
(b) a polypeptide having at least 99.5% identity to a polypeptide having an amino acid sequence as set out in amino acids 34 to 719 of SEQ ID NO: 2; or
(c) an amino acid sequence encoded by the polynucleotide as set out in nucleotides 100 to 2157 of SEQ ID NO: 1 or 3,
comprises the use of *Alicyclobacillus pohliae* NCIMB14276.

The alpha-amylase according to the invention is a starch degrading enzyme. Alpha-amylase activity can suitably be determined using the CERALPHA® procedure for measurement of alpha-amylase, which is recommend by the American Association of Cereal Chemists (AACC).

A lipolytic enzyme, also referred to herein as lipase, is an enzyme that hydrolyses triacylglycerol and/or galactolipid and or phospholipids.

Lipase activity may be determined spectrophotometrically by using the chromogenic substrate p-nitrophenyl palmitate (pNPP, Sigma N-2752). In this assay the pNPP is dissolved in 2-propanol (40 mg pNPP per 10 ml 2-propanol (Merck 1.09634)) and suspended in 100 mM Acetate buffer pH=5.0 containing 1.0% Triton X-100 (Merck 1.12298) (5 ml substrate in 45 ml buffer). The final substrate concentration is 1.1 mM. The lipase is incubated with this substrate solution at 37° C. for 10 minutes. The reaction is stopped by addition of stop buffer 2% TRIS (Merck 1.08387)+1% Triton X-100 in a 1:1 ratio with respect to the reaction mixture and subsequently the formed p-nitrophenol (pNP) is measured at 405 nm. This assay can also be applied at different pH values in order to determine pH dependence of a lipase. It should be understood that at different pH values different buffers might be required or that different detergents might be necessary to emulsify the substrate. One lipase unit is defined as the amount of enzyme that liberates 1 micromole of p-nitrophenol per minute at the reaction conditions stated. It should be understood that it is not uncommon practice in routine analysis to use standard calibration enzyme solutions with known activity determined in a different assay to correlate activity a given assay with units as would be determined in the calibration assay.

Alternatively, lipase activity may be determined by using 2,3-mercapto-1-propanol-tributyrate (TBDMP) as a substrate. Lipase hydrolyses the thioester bond(s) of TBDMP thereby liberating butanoic acid and 2,3-mercapto-1-propanol-dibutyrate, 2,3-mercapto-1-propanol-monobutyrate or 2,3-mercapto-1-propanol. The liberated thiol groups are titrated in a subsequent reaction with 4,4,-dithiodipyridine (DTDP) forming 4-thiopyridone. The latter is in a tautomeric equilibrium with 4-mercapthopyridine which absorbs at 334 nm. The reaction is carried out in 0.1 M acetate buffer pH 5.0 containing 0.2% Triton-X100, 0.65 mM TBDMP and 0.2 mM DTDP at 37° C. One lipase unit is defined as the amount of enzyme that liberates 1 micromole of 4-thiopyridone per minute at the reaction conditions stated.

In addition to spectrophotometric measurement lipase activity may also be determined using titrimetric measurement. For example the esterase activity of a lipolytic enzyme may be measured on tributyrin as a substrate according to Food Chemical Codex, Forth Edition, National Academy Press, 1996, p 803.

A phospholipase is an enzyme that catalyzes the release of fatty acyl groups from a phospholipid. It may be a phospholipase A2 (PLA2, EC 3.1.1.4) or a phospholipase A1 (EC 3.1.1.32). It may or may not have other activities such as triacylglycerol lipase (EC 3.1.1.3) and/or galactolipase (EC 3.1.1.26) activity.

The phospholipase may be a native enzyme from mammalian or microbial sources. An example of a mammalian phospholipase is pancreatic PLA2, e.g. bovine or porcine PLA2 such as the commercial product Lecitase 10L (porcine PLA2, product of Novozymes A/S).

Microbial phospholipases may be from *Fusarium*, e.g. *F. oxysporum* phospholipase A1 (WO 1998/026057), *F. venenatum* phospholipase A1 (described in WO 2004/097012 as a phospholipase A2 called FvPLA2), from *Tuber*, e.g. *T. borchii* phospholipase A2 (called TbPLA2, WO 2004/097012).

The phospholipase may also be a lipolytic enzyme variant with phospholipase activity, e.g. as described in WO 2000/032758 or WO 2003/060112.

The phospholipase may also catalyze the release of fatty acyl groups from other lipids present in the dough, particularly wheat lipids. Thus, the phospholipase may have triacylglycerol lipase activity (EC 3.1.1.3) and/or galactolipase activity (EC 3.1.1.26). The phospholipase may be a lipolytic enzyme as described in WO2009/106575, such as the commercial product PANAMORE® lipolytic enzyme, product of DSM.

The term 'baked product' refers to a baked food product prepared from a dough. Examples of baked products, whether of a white, brown or whole-meal type, which may be advantageously produced by the present invention include bread (in particular white, whole-meal or rye bread), typically in the form of loaves or rolls, French baguette-type bread, pastries, croissants, brioche, panettone, pasta, noodles (boiled or (stir-) fried), pita bread and other flat breads, tortillas, tacos, cakes, pancakes, cookies in particular biscuits, doughnuts, including yeasted doughnuts, bagels, pie crusts, steamed bread, crisp bread, brownies, sheet cakes, snack foods (e.g., pretzels, tortilla chips, fabricated snacks, fabricated potato crisps).

Baked product includes without limitation tin bread, loaves of bread, twists, buns, such as hamburger buns or steamed buns, chapati, rusk, dried steam bun slice, bread crumb, matzos, focaccia, melba toast, zwieback, croutons, soft pretzels, soft and hard bread, bread sticks, yeast leavened and chemically-leavened bread, laminated dough products such as Danish pastry, croissants or puff pastry products, muffins, danish, bagels, confectionery coatings, crackers, wafers, pizza crusts, tortillas, pasta products, crepes, waffles, parbaked products and refrigerated and frozen dough products.

An example of a parbaked product includes, without limitation, partially baked bread that is completed at point of sale or consumption with a short second baking process.

The bread may be white or brown pan bread; such bread may for example be manufactured using a so called American style Sponge and Dough method or an American style Direct method.

The term "dough" is defined herein as a mixture of flour and other ingredients. In one aspect the dough is firm enough to knead or roll. The dough may be fresh, frozen, prepared or parbaked. The preparation of frozen dough is described by Kulp and Lorenz in Frozen and Refrigerated Doughs and Batters.

Dough is made using dough ingredients, which include without limitation (cereal) flour, a lecithin source including egg, water, salt, sugar, flavours, a fat source including butter, margarine, oil and shortening, baker's yeast, chemical leavening systems such as a combination of an acid (generating compound) and bicarbonate, a protein source including milk, soy flour, oxidants (including ascorbic acid, bromate and Azodicarbonamide (ADA)), reducing agents (including L-cysteine), emulsifiers (including mono/di glycerides such as glycerol monostearate (GMS), sodium stearoyl lactylate (SSL), calcium stearoyl lactylate (CSL), polyglycerol esters of fatty acids (PGE) and DATEM), gums (including guargum and xanthangum), flavours, acids (including citric acid, propionic acid), starch, modified starch, gluten, humectants (including glycerol) and preservatives.

Cereals include maize, rice, wheat, barley, sorghum, millet, oats, rye, triticale, buckwheat, quinoa, spelt, einkorn, emmer, durum and kamut.

Dough is usually made from basic dough ingredients including (cereal) flour, such as wheat flour or rice flour, water and optionally salt. For leavened products, primarily baker's yeast is used next to chemical leavening systems such as a combination of an acid (generating compound) and bicarbonate.

The term dough herein includes a batter. A batter is a semi-liquid mixture, being thin enough to drop or poor from a spoon, of one or more flours combined with liquids such as water, milk or eggs used to prepare various foods, including cake.

The dough may be made using a mix including a cake mix, a biscuit mix, a brownie mix, a bread mix, a pancake mix and a crepe mix.

The term dough includes frozen dough, which may also be referred to as refrigerated dough. There are different types of frozen dough; that which is frozen before proofing and that which is frozen after a partial or complete proofing stage. The frozen dough is typically used for manufacturing baked products including without limitation biscuits, breads, bread sticks and croissants.

The invention also relates to the use of the alpha-amylase according to the invention in a number of industrial processes. Despite the long-term experience obtained with these processes, the alpha-amylase according to the invention may feature advantages over the enzymes currently used. Depending on the specific application, these advantages may include aspects like lower production costs, higher specificity towards the substrate, less antigenic, less undesirable side activities, higher yields when produced in a suitable microorganism, more suitable pH and temperature ranges, better tastes of the final product as well as food grade and kosher aspects.

In an embodiment the alpha-amylase according to the invention may be used in the food industry, including in food manufacturing.

An example of an industrial application of the alpha-amylase enzyme according to the invention in food is its use in baking applications. The alpha-amylase according to the invention may for example be used in baked products such as bread or cake. For example to improve quality of the dough and/or the baked product.

Therefore in one embodiment of the invention provides the use of the alpha-amylase according to the invention in the preparation of a dough and provides a dough comprising the alpha-amylase according to the invention. The invention also provides the preparation of a dough comprising the steps of adding the alpha-amylase according to the invention to at least one dough ingredient.

Yeast, enzymes and optionally additives are generally added separately to the dough.

Enzymes may be added in a dry, e.g. granulated form or in liquid form. Additives are in most cases added in powder form. Suitable additives include oxidants (including ascorbic acid, bromate and Azodicarbonamide (ADA)), reducing agents (including L-cysteine), emulsifiers (including mono/di glycerides such as glycerol monostearate (GMS), sodium stearoyl lactylate (SSL), calcium stearoyl lactylate (CSL), polyglycerol esters of fatty acids (PGE) and DATEM), gums (including guargum and xanthangum), flavours, acids (including citric acid, propionic acid), starch, modified starch, gluten, humectants (including glycerol) and preservatives.

The preparation of a dough from the dough ingredients is well known in the art and includes mixing of said ingredients and optionally one or more moulding and fermentation steps.

The preparation of baked products from such doughs is also well known in the art and may comprise moulding and shaping and further fermentation of the dough followed by baking at required temperatures and baking times. In one embodiment the invention provides a method to prepare a baked product comprising the step of baking the dough according to the invention. The baking of the dough to produce a baked product may be performed using methods well known in the art. The invention also provides a baked product obtainable according to this method. In an embodiment the baked product according to the invention is bread or cake. In one aspect of the invention, the alpha-amylase according to the invention may be used to prepare laminated doughs for baked products with improved crispiness.

The present invention also relates to methods for preparing a dough or a baked product comprising incorporating into the dough an effective amount of the alpha-amylase according to the invention, which improves one or more properties of the dough or the baked product obtained from the dough relative to a dough or a baked product in which the polypeptide is not incorporated.

The phrase "incorporating into the dough" is defined herein as adding the alpha-amylase enzyme according to the invention to the dough, any ingredient from which the dough is to be made, and/or any mixture of dough ingredients from which the dough is to be made. In other words, the alpha-amylase enzyme according to the invention may be added in any step of the dough preparation and may be added in one, two or more steps. The alpha-amylase enzyme according to the invention is added to the ingredients of a dough that is kneaded and baked to make the baked product using methods well known in the art. See, for example, U.S. Pat. No. 4,567,046, EP-A-426,211, JP-A-60-78529, JP-A-62-111629, and JP-A-63-258528.

The term "effective amount" is defined herein as an amount of the alpha-amylase according to the invention that is sufficient for providing a measurable effect on at least one property of interest of the dough and/or baked product. A suitable amount is in a range of 10-20000 MU units/kg flour, in an embodiment 100-2000 MU/kg flour, in a further embodiment 200-1000 MU/kg flour. A suitable amount includes 1 ppm-2000 ppm of an enzyme having an activity in a range of about 10.000 to 12.000. In an embodiment an effective amount is in a range of 10-200 ppm of an enzyme having an activity in a range of about 10,000 to 12.000, in another embodiment 20-80 ppm of an enzyme having an activity in a range of about 10.000 to 12.000. In an embodiment an effective amount is in a range of 10-200 ppm of an enzyme having an activity of about 10.000 MU/g. Herein and hereinafter MU stands for Maltotriose Unit as defined in the examples under the heading Maltotriose Assay (MU Assay).

The term "improved property" is defined herein as any property of a dough and/or a product obtained from the dough, particularly a baked product, which is improved by the action of the alpha-amylase enzyme according to the invention relative to a dough or product in which the alpha-amylase enzyme according to the invention is not incorporated. The improved property may include, but is not limited to, increased strength of the dough, increased elasticity of the dough, increased stability of the dough, reduced stickiness of the dough, improved extensibility of the dough, improved machineability of the dough, increased volume of the baked product, improved flavour of the baked product, improved crumb structure of the baked product, improved crumb softness of the baked product, reduced blistering of the baked product, improved crispiness, improved resilience both initial and in particular after storage, reduced hardness after storage and/or improved anti-staling of the baked product.

The improved property may be determined by comparison of a dough and/or a baked product prepared with and without addition of the (isolated) polypeptide of the present invention in accordance with the methods of present invention which are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to forming faults as a consequence of mechanical abuse thus better maintaining its shape and volume and is evaluated by the ratio of height:width of a cross section of a loaf after normal and/or extended proof.

The term "reduced stickiness of the dough" is defined herein as the property of a dough that has less tendency to adhere to surfaces, e.g., in the dough production machinery, and is either evaluated empirically by the skilled test baker or measured by the use of a texture analyser (e.g. a TAXT Plus) as known in the art.

The term "improved extensibility of the dough" is defined herein as the property of a dough that can be subjected to increased strain or stretching without rupture.

The term "improved machineability of the dough" is defined herein as the property of a dough that is generally less sticky and/or more firm and/or more elastic. Consequently there is less fouling of plant equipment and a reduced need for cleaning.

The term "increased volume of the baked product" is preferably measured as the volume of a given loaf of bread determined by an automated bread volume analyser (eg. BVM-3, TexVol Instruments AB, Viken, Sweden), using ultrasound or laser detection as known in the art. In case the volume is increased, the property is improved. Alternatively the height of the baked product after baking in the same size tin is an indication of the baked product volume. In case the height of the baked product has increased, the volume of the baked product has increased.

The term "reduced blistering of the baked product" is defined herein as a visually determined reduction of blistering on the crust of the baked bread.

The term "improved crumb structure of the baked product" is defined herein as the property of a baked product with finer cells and/or thinner cell walls in the crumb and/or more uniform/homogenous distribution of cells in the crumb and is usually evaluated visually by the baker or by digital image analysis as known in the art (eg. C-cell, Calibre Control International Ltd, Appleton, Warrington, UK).

The term "improved softness of the baked product" is the opposite of "hardness" and is defined herein as the property of a baked product that is more easily compressed and is evaluated either empirically by the skilled test baker or measured by the use of a texture analyzer (e.g. TAXT Plus) as known in the art.

The term "improved flavor of the baked product" is evaluated by a trained test panel.

The term "improved anti-staling of the baked product" is defined herein as the properties of a baked product that have a reduced rate of deterioration of quality parameters, e.g. reduced hardness after storage and/or decreased loss of resilience after storage.

Anti-staling properties may be demonstrated by a reduced hardness after storage of the baked product. The alpha-amylase according to the invention may result in reduced hardness, e.g. in a baked product that is more easily compressed. The hardness of the baked product may be evaluated either empirically by the skilled test baker or measured by the use of a texture analyzer (e.g. TAXT Plus) as known in the art. The hardness measured within 24 hours after baking is called initial hardness. The hardness measured 24 hours or more after baking is called hardness after storage, and is also a measure for determining shelf life. In case the initial hardness has reduced, it has improved. In case the hardness after storage has reduced, it has improved. Preferably hardness is measured as described in example 9 herein.

Resilience of the baked product is preferably measured by the use of a texture analyzer (e.g. TAXTPlus) as known in the art.

The resilience measured within 24 hours after baking is called initial resilience. The resilience measured 24 hours or more after baking is called resilience after storage, and is also a measure for determining shelf life. Freshly baked product typically gives crumb of high initial resilience but resilience is lost over shelf-life. Improved anti-staling properties may be demonstrated by a reduced loss of resilience over storage. Preferably resilience is measured as described in example 9 herein.

The term "improved crispiness" is defined herein as the property of a baked product to give a crispier sensation than a reference product as known in the art, as well as to maintain this crispier perception for a longer time than a reference product. This property can be quantified by measuring a force versus distance curve at a fixed speed in a compression experiment using e.g. a texture analyzer TA-XT Plus (Stable Micro Systems Ltd, Surrey, UK), and obtaining physical parameters from this compression curve, viz. (i) force of the first peak, (ii) distance of the first peak, (iii) the initial slope, (iv) the force of the highest peak, (v) the area under the graph and (vi) the amount of fracture events (force drops larger than a certain preset value). Indications of improved crispness are a higher force of the first peak, a shorter distance of the first peak, a higher initial slope, a higher force of the highest peak, higher area under the graph and a larger number of fracture events. A crispier product should score statistically significantly better on at least two of these parameters as compared to a reference product. In the art, "crispiness" is also referred to as crispness, crunchiness or crustiness, meaning a material with a crispy, crunchy or crusty fracture behaviour.

The present invention may provide a dough having at least one of the improved properties selected from the group consisting of increased strength, increased elasticity, increased stability, reduced stickiness, and/or improved extensibility of the dough.

The invention also may provide a baked product having increased loaf volume. The invention may provide as well a baked product having at least one improved property selected from the group consisting of increased volume, improved flavour, improved crumb structure, improved crumb softness, improved crispiness, reduced blistering and/or improved anti-staling.

The alpha-amylase according to the invention may be used for retarding staling of a baked product such as bread and cake. Retarding of staling may be indicated by a reduced hardness, in particular a reduced hardness after storage compared to a baked product, including bread and cake, that is produced without the alpha-amylase according to the invention according to the invention.

The alpha-amylase according to the invention has an intermediate thermostability compared with other alpha-amylases used in the industry. The alpha-amylase of the invention has higher temperature stability than fungal alpha-amylase or alpha amylase from cereal flour. On the other hand, it has a lower thermostability at high temperature, in particular a lower thermostability at the inactivation temperature of the alpha-amylase during baking, than other amylases used in the industry, such as bacterial alpha-amylase.

The alpha-amylase according to the invention has a lower thermostability at a high temperature, in an embodiment at a temperature above 70° C., preferably at a temperature above 75° C., preferably at a temperature above 78° C., preferably at a temperature above 80° C., preferably at a temperature above 82° C., preferably at a temperature above 85° C., compared to known alpha-amylases as measured using a method as described in example 8 herein. Preferably thermostability is evaluated as follows: 25 MU/ml purified enzyme solution in a buffer containing 50 mM sodium acetate, pH 5.0, 1 mM $CaCl_2$ and 1 g/L BSA are pre-incubated in an Eppendorf tube for 30 minutes at various temperatures (40° C. to 86° C.). The residual enzyme activity is determined using the MU assay described herein in the examples under "Determination of enzyme activity", "2) Maltotriose assay (MU assay)".

The alpha-amylase enzyme according to the invention is preferably active during baking and is preferably inactivated before end of baking.

Benefits of the alpha-amylase according to the invention having an intermediate thermostability and/or a lower thermostability at a high temperature, may include, without limitation, one or more of the following.

An enzyme having lower thermostability at a high temperature may result in an increased level of denaturation of the enzyme during the baking process. This may result in a more complete inactivation of the enzyme activity and thus impart greater control of enzyme function in the baking process.

It has been observed that small and large baked products have different heat transfer rates, different bake times and consequently different thermal treatments. The alpha-amylase according to the invention may be beneficial for baked products undergoing less thermal treatment as a consequence of reduced baking time and/or temperature.

It has been observed that bread baked at a higher altitude such as locations above 2000 m (e.g. Mexico City 2240 m altitude) may suffer from difficulties in achieving crumb temperatures sufficient to inactivate thermostable enzymes. Without being bound to theory, it is thought that this is because the water boils at a lower temperature due to the lower atmospheric pressure, and this dictates the maximum temperature reached in the centre of a baked product. A lower maximum temperature in the centre of the baked product may make it more difficult to (fully) inactivate the enzyme. An alpha-amylase having lower thermostability at high temperature might confer advantage in such locations, such as Mexico City, for example.

Industrial bakeries are under increasing pressure to reduce baking times and oven temperatures—often to below 20 minutes, both for cost benefit and for sustainability reasons. A more heat labile enzyme may be better suited to a shorter baking time in that the enzyme is more effectively denatured at the end of the baking process. Parbaked bread receives a shorter baking time—e.g. typically 20% shorter baking process and/or 10° C. lower oven temperature than full baked equivalents, and may therefore also be expected to benefit from an enzyme having lower thermostability at high temperatures.

The alpha-amylase enzyme of the present invention and/or additional enzymes to be used in the methods of the present invention may be in any form suitable for the use in question, e.g. in the form of a dry powder, agglomerated powder or granulate, in particular a non-dusting granulate, liquid, in particular a stabilized liquid, or protected enzyme such described in WO01/11974 and WO02/26044. A liquid form includes without limitation an emulsion, a suspension and a solution. Granulates and agglomerated powders may be prepared by conventional methods, e.g. by spraying the alpha-amylase enzyme according to the invention onto a carrier in a fluid-bed granulator. The carrier may consist of particulate cores having a suitable particle size. The carrier may be soluble or insoluble, suitable carriers include a salt (such as NaCl or sodium sulphate), sugar alcohol (such as sorbitol), starch, rice flour, wheat flour, corn grits, maltodextrins or soy.

Such granulate or agglomerated powder, comprising the polypeptide of the present invention, may be referred to as a baking additive. The baking additive preferably has a narrow particle size distribution with more than 95% (by weight) of the particles in the range from 25 to 500 μm.

The amylolytic enzyme according to the invention and/or additional enzymes may be contained in slow-release formulations. Methods for preparing slow-release formulations are well known in the art. Adding nutritionally acceptable stabilizers such as sugar, sugar alcohol, or another polyol, and/or lactic acid or another organic acid according to established methods may for instance, stabilize liquid enzyme preparations.

Preferably the enzyme according to the invention is provided in a dry form, to allow easy handling of the product. Irrespective of the formulation of the enzyme, the formulation may comprise one or more additives. Examples of suitable additives include oxidants (including ascorbic acid, bromate and Azodicarbonamide (ADA)), reducing agents (including L-cysteine), emulsifiers (including mono/di glycerides such as glycerol monostearate (GMS), sodium stearoyl lactylate (SSL), calcium stearoyl lactylate (CSL), polyglycerol esters of fatty acids (PGE) and DATEM), gums (including guargum and xanthangum), flavours, acids (including citric acid, propionic acid), starch, modified starch, gluten, humectants (including glycerol) and preservatives.

The alpha-amylase enzyme according to the invention may also be incorporated in yeast comprising compositions such as disclosed in EP-A-0619947, EP-A-0659344 and WO02/49441.

For inclusion in a pre-mix of flour it is advantageous that the (isolated) polypeptide according to the invention is in the form of a dry product, e.g., a non-dusting granulate, whereas for inclusion together with a liquid it is advantageously in a liquid form.

One or more additional enzymes may also be incorporated into the dough. Therefore the invention provides an enzyme composition comprising the alpha-amylase enzyme according to the invention and one or more additional enzymes. The enzyme composition may be a baking enzyme composition. This enzyme composition may be used in dough products and baked products obtained from such dough. For example it may used in dough products further containing eggs and in baked products, such as brioche and panettone, both regular and with a reduced amount of eggs. The additional enzyme may be of any origin, including mammalian and plant, and preferably of microbial (bacterial, yeast or fungal) origin and may be obtained by techniques conventionally used in the art.

In an embodiment, the additional enzyme may be an amylase, including a further alpha-amylase, such as an fungal alpha-amylase (which may be useful for providing sugars fermentable by yeast and retarding staling), beta-amylase, a cyclodextrin glucanotransferase, a protease, a peptidase, in particular, an exopeptidase (which may be useful in flavour enhancement), transglutaminase, triacyl glycerol lipase (which may be useful for the modification of lipids present in the dough or dough constituents no as to soften the dough), galactolipase, phospholipase, cellulase, hemicellulase, in particular a pentosanase such as xylanase (which may be useful for the partial hydrolysis of pentosans, more specifically arabinoxylan, which increases the extensibility of the dough), protease (which may be useful for gluten weakening in particular when using hard wheat flour), protein disulfide isomerase, e.g., a protein disulfide isomerase as disclosed in WO 95/00636, glycosyltransferase, peroxidase (which may be useful for improving the dough consistency), laccase, or oxidase, hexose oxidase, e.g., a glucose oxidase, aldose oxidase, pyranose oxidase, lipoxygenase or L-amino acid oxidase (which may be useful in improving dough consistency) or a protease.

The cellulase may be from *A. niger* or from *Trichoderma reesei*.

The amyloglucosidase, may be an amyloglucosidase from *Aspergillus* such as from *A. oryzae* or *A. niger*, preferably from *A. niger*.

In an embodiment the additional enzyme is a lipolytic enzyme, including a triacyl glycerol lipase, a phospholipase, a galactolipase and an enzyme having both galactolipase and phospholipase activity.

The triacyl glycerol lipase may be a fungal lipase, preferably from *Rhizopus, Aspergillus, Candida, Penicillum, Thermomyces*, or *Rhizomucor*. In an embodiment the triacyl glycerol lipase is from *Rhyzopus*, in a further embodiment a triacyl glycerol lipase from *Rhyzopus oryzae* is used. Optionally a combination of two or more triacyl glycerol lipases may be used.

In a further embodiment the lipolytic enzyme is a phospholipase or an enzyme having both galactolipase and phospholipase activity. Such lipases are known to be active on the endogenous lipids of wheat and on extraneous lipid sources, for example as provided by added shortening fat or from lecithin. Preferentially the lipase cleaves polar lipids and has phospholipase activity, galactolipase activity or a combination of phospholipase and galactolipase activity to create lysophospholipids, such as lysophoshotidyl choline, and lysogalactolipids such as digalactosylmonoglyceride. The specificity of the lipase can be shown through in vitro assay making use of appropriate substrate, for example triacylglycerol lipid, phosphotidylcholine and diglactosyldiglyceride, or preferably through analysis of the reactions products that are generated in the dough during mixing and fermentation.

PANAMORE® lipolytic enzyme, LIPOPAN® lipase, LIPOPAN® 50 lipase, AND LIPOPAN® S lipase are commercialised to standardised lipolytic activity, using a measurement of DLU for Panamore® from DSM and a measurement of LU for the LIPOPAN® family of lipases from Novozymes. DLU is defined as the amount of enzyme needed to produce 1 micromol/min of p-nitrophenol from p-nitrophenyl palmitate at pH 8.5 at 37° C., while LU is defined as the amount of enzyme needed to produce 1 micromol/min of butyric acid from tributyrin at pH 7 at 30° C. Lipases are optimally used with the alpha-amylase of the invention at 2-850 DLU/kg flour or at 50-23500 LU/kg flour.

In an embodiment of the enzyme composition according to the invention the additional enzyme is PANAMORE® lipolytic enzyme as described in WO2009/106575.

In an embodiment of the enzyme composition of the invention the additional enzyme is an enzyme as described in WO9826057.

In an aspect of the enzyme composition according to the invention the additional enzyme is an enzyme as described in U.S. RE38,507.

In an aspect of the enzyme composition according to the invention the additional enzyme is an enzyme as described in WO 9943794, in particular in EP1058724B1.

If one or more additional enzyme activities are to be added in accordance with the methods of the present invention, these activities may be added separately or together with the polypeptide according to the invention, for example as the enzyme composition according to the invention, which includes a bread-improving composition and/or a dough-improving composition. The other enzyme activities may be any of the enzymes described above and may be dosed in accordance with established baking practices.

In an embodiment the enzyme composition according to the invention is provided in a dry form, to allow easy addition to the dough, the dough ingredients, but liquid forms are also possible. A liquid form includes without limitation an emulsion, a suspension and a solution. Irrespective of the formulation of the enzyme composition, any additive or additives known to be useful in the art to improve and/or maintain the enzyme's activity, the quality of the dough and/or the baked product may be applied. Examples of suitable additives include oxidants (including ascorbic acid, bromate and Azodicarbonamide (ADA)), reducing agents (including L-cysteine), emulsifiers (including mono/di glycerides such as glycerol monostearate (GMS), sodium stearoyl lactylate (SSL), calcium stearoyl lactylate (CSL), polyglycerol esters of fatty acids (PGE) and DATEM), gums (including guargum and xanthangum), flavours, acids (including citric acid, propionic acid), starch, modified starch, gluten, humectants (including glycerol) and preservatives.

The alpha-amylase according to the invention may be incorporated in a pre-mix, e.g. in the form of a flour composition, for dough and/or baked products made from dough, in which the pre-mix comprises a polypeptide of the present invention. The term "pre-mix" is defined herein to be understood in its conventional meaning, i.e. as a mix of baking agents, generally including flour, which may be used not only in industrial bread-baking plants/facilities, but also in retail bakeries. The pre-mix may be prepared by mixing the alpha-amylase according to the invention or the enzyme composition according to the invention with a suitable carrier such as flour, starch or a salt. The pre-mix may contain additives as mentioned above.

In another aspect, the alpha-amylase enzyme according to the invention may be used in the production of cake and in the production of a batter from which a cake can be made.

The alpha-amylase enzyme according to the invention may be used in the preparation of a wide range of cakes, including shortened cakes, such as for example pound cake and butter cake, and including foam cakes, such as for example meringues, sponge cake, biscuit cake, roulade, genoise and chiffon cake. Sponge cake is a type of soft cake based on wheat flour, sugar, baking powder and eggs (and optionally baking powder). The only fat present is from the egg yolk, which is sometimes added separately from the white. It is often used as a base for other types of cakes and desserts. A pound cake is traditionally prepared of one pound each of flour, butter, eggs, and sugar, optionally complemented with baking powder. In chiffon cake the butter/margarine has been replaced by oil. Sugar and egg yolk content has been decreased compared to pound or sponge cake and egg white content has been increased.

A method to prepare a batter preferably comprises the steps of:
  a. preparing the batter of the cake by adding at least:
    i. sugar;
    ii. flour;
    iii. the alpha-amylase enzyme according to the invention;
    iv. at least one egg; and
    v. optionally a phospholipase.

A method to prepare a cake according to the invention further comprises the step of
  b. baking the batter to yield a cake.

The person skilled in the art knows how to prepare a batter or a cake starting from dough ingredients. Optionally one or more other ingredients can be present in the composition e.g. to allow reduction of eggs and/or fat in the cake, such as hydrocolloids, yeast extract, calcium.

The above-mentioned industrial applications of the alpha-amylase enzyme according to the invention comprise only a few examples and this listing is not meant to be restrictive.

Other uses of the alpha-amylase according to the invention may include:
  the production of glucose, fructose and maltose syrups;
  production of starch hydrolysates such as maltodextrins;
  production of modified starches;
  modification of starch components in animal feed; and/or
  replacement of malt in brewing.

EXAMPLES

Determination of Enzyme Activity
1) AACC Method 22-02.01
Measurement of Alpha-Amylase in Plant and Microbial Materials Using the CERALPHA® Method for Measurement of Alpha-Amylase The alpha-amylase activity was quantified by measuring activity using a Megazyme CERALPHA alpha-amylase assay kit (Megazyme International Ireland Ltd., Co. Wicklow, Ireland) according to the manufacturer's instruction.
2) Maltotriose Assay (MU Assay)

One Maltotriose Unit (MU) is defined as the amount of enzyme that liberates 1 μmole glucose per minute using maltotriose substrate under the following assay conditions. Enzymatic activity was determined at 37° C. and pH 5.0 using maltotriose as substrate. Enzymatic hydrolysis of maltotriose results in quantitative release of glucose, which is a measure for enzymatic activity. The final assay concentrations: 8 mg/ml maltotriose, 0.007 to 0.02 MU/ml mature DSM-AM, 20 mM citrate buffer, 0.2 mg/ml BSA, 2 mM NaCl. The reaction was stopped after 30 minutes (addition of 0.33 M NaOH in 1:10 ratio) and the released glucose was converted into gluconate-6-P in two steps during which NADH is formed, using a Glucose Hexokinase FS kit (Diagn. Syst). The resulting absorbance increases at a wavelength of 340 nm was a measure for the amount of glucose released during the 30 minute incubation. Activity was calculated using a glucose calibration line.

Example 1

Production of the Alpha-Amylase of the Invention

Cloning and Enzyme Preparation
As described in further detail below the alpha-amylase gene was cloned and expressed in *B. subtilis* in the following way
Strains and Plasmids
*Bacillus subtilis* strain BS154 (CBS 363.94) (ΔaprE, ΔnprE, amylE, spo-) is described in Quax and Broekhuizen 1994 Appl Microbiol Biotechnol. 41: 425-431.
The *E. coli/B. subtilis* shuttle vector pBHA12 is described in (WO2008/000632).
*Alicyclobacillus pohliae* NCIMB14276 was described by Imperio et al (int. J, Syst. Evol. Microbiol 58:221-225, 2008).

*Bacillus stearothermophilus* C599 (NCIMB11873) is described in WO91/04669.

Molecular Biology Techniques

Molecular biology techniques known to the skilled person were performed (see: Sambrook & Russell, Molecular Cloning: A Laboratory Manual, 3rd Ed., CSHL Press, Cold Spring Harbor, N.Y., 2001). Polymerase chain reaction (PCR) was performed on a thermocycler with Phusion High-Fidelity DNA polymerase (Finnzymes OY, Aspoo, Finland) according to the instructions of the manufacturer.

Amylase Activity

Alpha-amylase activity in the broth of *B. subtilis* cultures was quantified as described above according to AACC Method 22-02.01.

Sequencing of *Alicyclobacillus pohliae* Genome

The genome of *Alicyclobacillus pohliae* NCIMB14276 was sequenced by BaseClear (Leiden, The Netherlands). The DNA was fragmented (shearing) and DNA adapters were ligated to both ends of the DNA fragments. Two sets of Illumina GAIIx sequence reads were obtained. One set consisted of paired-end reads, spanning a distance of around 250 (+−125) nucleotides. The second set consisted of mate pair reads, spanning a distance of around 4200 nucleotides (+−2100). On all Illumina GAIIx sequence reads a quality filtering was applied based on Phred quality scores. In addition, low quality and ambiguous nucleotides were trimmed off from the remaining reads. The filtered paired-end and mate pair reads were used for 'De novo' assembly in the CLC Genomics Workbench version 4.6.1 or 4.7 (CLC bio, Aarhus, Denmark). In this way, a set of pre-assembled contigs (contiguous sequences) were obtained. The contigs were arranged further (scaffolding) using SSPACE described by Boetzer et al. (Bioinformatics 27:578-579, 2011). The sequence analysis revealed that the *Alicyclobacillus pohliae* NCIMB14276 genome contains a gene encoding an alpha-amylase enzyme named DSM-AM herein with the nucleotide sequence as set out in SEQ ID NO: 1, see also FIG. 3.

The corresponding DSM-AM protein encoded by SEQ ID NO.1 has the amino acid sequence as set out in SEQ ID NO: 2, see also FIG. 4.

The nucleotide sequence of the codon optimized DSM-AM gene out in SEQ ID NO: 3, see also FIG. 5.

Example 2

Expression of *A. pohliae* DSM-AM Gene in *Bacillus subtilis*

An amyQ terminator and a PmeI restriction site were introduced in the pBHA12 vector by digesting pBHA12 with SphI and HindIII and cloning the following DNA sequence (SEQ ID NO:4): 5'-GCATGCGTTAAACAAA AACACCTC-CAAGCTGAGTGCGGGTATCAGCTTGGAG-GTGCGTTTATTTTTCA GCCGTATGACAAGGTCG-GCATCAGAAGCTT-3' (the 5' SphI and 3' HindIII restriction sites are underlined).

The fragment was cloned into pBHA12 which resulted in vector pGBB09 (FIG. 1).

Figure 2:
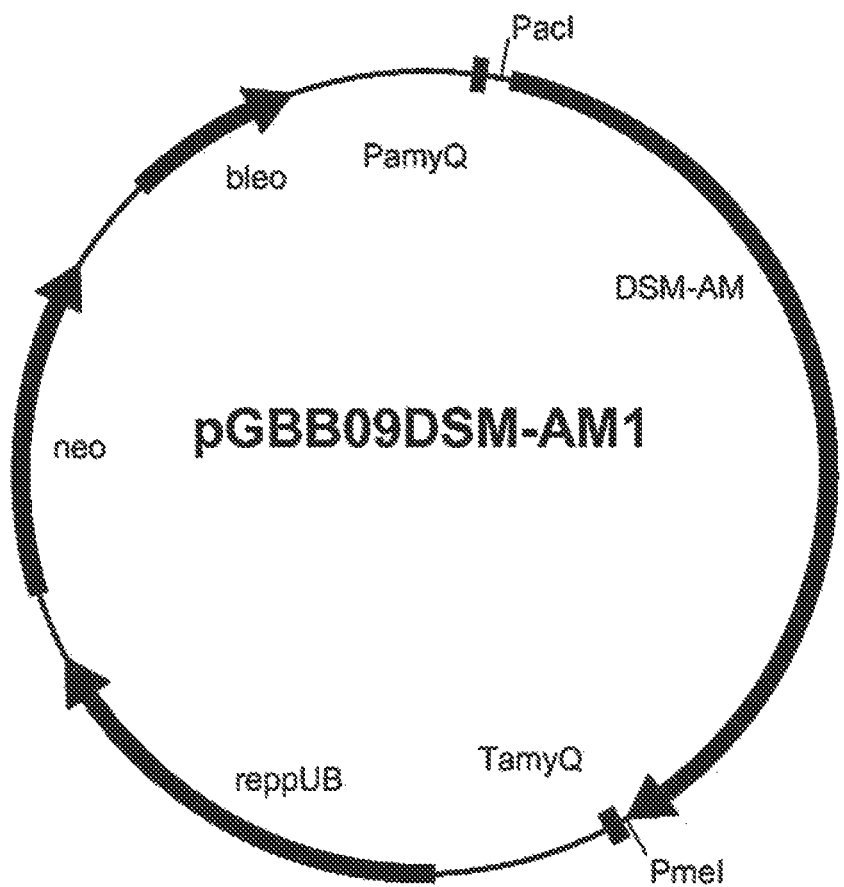
FIG. 2 sets out the plasmid map of pGBB09DSM-AM1.

The DSM-AM gene was synthesised by GeneArt (Germany) and at the 5' end the PacI restriction site was added and at its 3' end the PmeI restriction site was added. The DSM-AM gene was cloned into the PacI and PmeI digested pGBB09 vector which resulted in vector pGBB09DSM-AM1 (FIG. 2). This vector was transformed to *B. subtilis* strain BS154. The sequence of the plasmid was confirmed by DNA sequencing. The *B. subtilis* strain BS154 containing pGBB09DSM-AM1 was named DSM-AMB154-1.

Example 3

Expression of DSM-AM with *B. subtilis* in Shake Flasks

*B. subtilis* strains DSM-AMB154-1 and BS154 were grown in a shake flask. These shake flasks contained 20 ml 2xTY medium composed of 1.6% (w/v) Bacto tryptone, (w/v) Yeast extract and 0.5% (w/v) NaCl. The cultures were shaken vigorously at 37° C. and 250 rpm for 16 hours and 0.2 ml culture medium was used to inoculate 20 ml SMM medium. SMM pre-medium contains 1.25% (w/w) yeast extract, 0.05% (w/w' CaCl2, 0.075% (w/w) MgCl2.6H2O, 15 μg/l MnSO4.4H2O, 10 μg/l CoCl2.6H2O, 0.05% (w/w) citric acid, 0.025% (w/w) antifoam 86/013 (Basildon Chemicals, Abingdon, UK). To complete SMM medium, 20 ml of 5% (v/v) maltose and 20 ml of a 200 mM Na-phosphate buffer stock solution (pH 6.8), both prepared and sterilized separately, were added to 60 ml SMM pre-medium. These cultures were incubated for 48 hours at 37° C. and 250 rpm. The supernatants were harvested and analysed for enzyme productivity. The alpha-amylase activity of strain DSM-AMB154-1 was measured according to AACC Method 22-02.01 as described in above. The supernatant of DSM-AMB154-1 contained alpha-amylase activity whereas the parent strain BS154 did not.

Example 4

Enzyme Preparation

*Bacillus* strain DSM-AMB154-1 was cultivated under aerobic conditions in a suitable fermentation medium.

The enzyme was secreted into the medium. The ensuing fermentation broth was filtered to remove bacterial cells, debris from these cells and other solids. The filtrate containing the enzyme, thus obtained, was then concentrated by ultrafiltration to yield a concentrate containing mature DSM-AM.

Example 5

Enzyme Purification

The purification was performed using of the following steps. The concentrated fermentation broth obtained in example 4 containing mature DSM-AM was mixed with 50 mM HEPES buffer, pH 7.5 containing 400 mg/ml (NH$_4$)$_2$SO4 (1:1 ratio). The solution was stirred overnight at 4° C., and followed by centrifugation at 3220 rcf, 4° C. for 10 minutes. The pellet was resuspended in 25 mM Tris buffer, pH7.5, and filtrated through 0.45 μm filter. The conductivity of the solution was adjusted to 2 ms/cm by addition of MilliQ water, and followed by pH adjustment to pH=7.5. The solution was concentrated by Vivaspin 20 ml Concentrator (Sartorius Stedim) 10.000MWCO, at 3220rcf, 4° C. for 15 min. The solution was applied to a Q-Sepharose column equilibrated with 25 mM HEPES buffer, pH 7.5. The protein was collected in flow-through. Flow-through was re-applied to a Q-sepharose column equilibrated with 25 mM HEPES buffer. pH 9.5. Protein was eluted with a 0-1 M NaCl gradient. The purified mature DSM-AM enzyme was desalted by a PD-10 desalting column (GE Healthcare) using 25 mM Tris buffer, pH7.5.

Protein Determination

The protein concentration of the purified mature DSM-AM enzyme as obtained in example 5 was determined by BCA™ protein assay kit (Pierce) according to the manufacturer's instruction with the following condition: the ratio of the sample to WR reagent was 1:12, and the absorbance of the mixture was determined at wavelength of 540 nm.

Example 6

Enzyme Properties

Dependence of the enzyme activity of the mature DSM-AM as obtained in example 5, on pH was tested by the MU assay described above using a reaction mixture in which pH was adjusted to different values (pH 4.0, 4.3, 5.0, 5.5, 6.0, 6.5, 7.0, 7.5). Two measurements with two final enzyme concentrations, 0.01 and 0.018 MU/ml were taken. The results were described as a relative activity. The pH optimum for mature DSM-AM was found to be at pH 5.0. The activities measured at the other indicated pH's are shown in the table below. The value corresponds to an average value of both measurements at different enzyme concentrations.

TABLE 6.1

| | pH | | | | | | | |
|---|---|---|---|---|---|---|---|---|
| | 4.0 | 4.3 | 5.0 | 5.5 | 6.0 | 6.5 | 7.0 | 7.5 |
| Relative activity | 68% | 76% | 100% | 87% | 71% | 40% | 21% | 8% |

Dependence of the mature DSM-AM enzyme activity on temperature was determined using the MU assay described above with the reaction temperatures set to 40° C., 50° C., 60° C., 65° C., 70° C., 75° C., 80° C. and 90° C. Mature DSM-AM was most active at 60-75° C. and the enzyme lost approximately 90% of its activity when the temperature was above 90° C.

Example 7

Alpha-Amylase Activity

The alpha-amylase activity of the mature DSM-AM as obtained in example 5, was quantified by measuring activity using a Megazyme CERALPHA alpha-amylase assay kit (Megazyme International Ireland Ltd., Co. Wicklow, Ireland) according to the manufacturer's instruction.

TABLE 7.1

| Sample | Activity | Activity in Ceralpha assay @ 40° C. | Activity in Ceralpha assay @ 60° C. |
|---|---|---|---|
| Mature DSM-AM | 1095 MU/ml | 124 U/ml | 191 U/ml |
| Control malt flour | Estimated 1.9 U/ml Estimated 36 U/ml | 2.8 U/ml | 43 U/ml |

Example 8

Thermostability of Mature DSM-AM

To evaluate the thermostability of the mature DSM-AM, as obtained in example 5, 25 MU/ml purified enzyme solution in a buffer containing 50 mM sodium acetate, pH 5.0, 1 mM CaCl2 and 1 g/L BSA were pre-incubated in an Eppendorf tube for 30 minutes at various temperatures (40° C. to 86° C.). The residual enzyme activity was determined using the MU assay described above. For comparison, NOVAMYL® antistaling agent was included. The results were expressed as a percentage of the activity of a sample that was pre-incubated for 30 minutes at 4° C.

In the temperature range from 40° C. to 75° C. comparable high-level activities (above 90%) were observed for mature DSM-AM and NOVAMYL® antistaling agent (data not shown). The residual enzyme activities from the temperature range of 76 to 86° C. are listed in the Table 8.1 below. These data clearly demonstrated that mature DSM-AM and NOVAMYL® antistaling agent are comparably thermostable at temperatures up to about 80° C. However, at the temperatures of about 80° C. and higher the residual enzymatic activity of mature DSM-AM is lower than that of NOVAMYL® antistaling agent.

TABLE 8.1

| | Enzyme activity | | | | | | |
|---|---|---|---|---|---|---|---|
| | Temperature [° C.] | | | | | | |
| | 4 | 76 | 78 | 80 | 82 | 84 | 86 |
| Mature DSM-AM | 100% | 91% | 85% | 69% | 38% | 14% | 1% |
| NOVAMYL ® | 100% | 87% | 82% | 72% | 54% | 31% | 10% |

NOVAMYL ® antistaling agent was obtained from Novozymes, Denmark.

To further evaluate the thermostability of the mature DSM-AM, as obtained in example 5, the residual activity of 7.5 MU/ml mature DSM-AM was tested in glass tube in a buffer of 50 mM sodium acetate, pH 4.3, 1 mM CaCl$_2$. After incubation at 80° C. for 15 minutes, the residual activity was determined as described above. Mature DSM-AM showed a residual activity of 3% whereas NOVAMYL® antistaling agent showed 13% residual activity at the same conditions. The results are listed in Table 8.2.

TABLE 8.2

| | Residual activity | |
|---|---|---|
| Temperature [° C.] | 4 | 80 |
| Mature DSM-AM | 100% | 3% |
| NOVAMYL ® | 100% | 13% |

NOVAMYL ® antistaling agent was obtained from Novozymes, Denmark.

The invention claimed is:

1. An isolated polynucleotide comprising:
   (a) SEQ ID NO:1 or SEQ ID NO:3; or
   (b) nucleotides 100 to 2157 of SEQ ID NO:1; or
   (c) nucleotides 100 to 2157 of SEQ ID NO:3; or
   (d) a polynucleotide sequence encoding a polypeptide comprising SEQ ID NO:2; or
   (e) a polynucleotide sequence encoding a polypeptide comprising amino acids 34 to 719 of SEQ ID NO:2.

2. The isolated polynucleotide according to claim 1, wherein the polynucleotide is produced by the method comprising:
   (a) obtaining the genome of *Alicyclobacillus pohliae* NCIMB14276;
   (b) performing sequence analysis on said genome, thereby identifying said polynucleotide in said genome; and
   (c) isolating said polynucleotide.

3. A vector comprising the isolated polynucleotide according to claim 1.

4. The vector according to claim 3 which is an expression vector, wherein the polynucleotide sequence is operably linked with at least one regulatory sequence allowing for expression of the polynucleotide sequence in a suitable host cell.

5. A method for manufacturing the polynucleotide according to claim 1 comprising culturing an isolated host cell transformed with said polynucleotide and isolating said polynucleotide from said host cell.

6. An isolated polypeptide comprising:
   (a) amino acids 34 to 719 of SEQ ID NO:2;
   (b) an amino acid sequence encoded by a polynucleotide comprising nucleotides 100 to 2157 of SEQ ID NO:1; or
   (c) an amino acid sequence encoded by a polynucleotide comprising nucleotides 100 to 2157 of SEQ ID NO:3.

7. A method of manufacturing the polypeptide according to claim 6 comprising cultivating an isolated host cell comprising a vector, the vector comprising a polynucleotide comprising:
   (a) SEQ ID NO:1 or SEQ ID NO:3; or
   (b) nucleotides 100 to 2157 of SEQ ID NO:1; or
   (c) nucleotides 100 to 2157 of SEQ ID NO:3; or
   (d) a polynucleotide sequence encoding a polypeptide comprising SEQ ID NO:2; or
   (e) a polynucleotide sequence encoding a polypeptide comprising amino acids 34 to 719 of SEQ ID NO:2,
   under conditions which allow for expression of the vector and, optionally, recovering the encoded polypeptide from the cell or culture medium.

8. A method of manufacturing the polypeptide according to claim 6 comprising cultivating an isolated host cell comprising a polynucleotide, said polynucleotide comprising:
   (a) SEQ ID NO:1 or SEQ ID NO:3; or
   (b) nucleotides 100 to 2157 of SEQ ID NO:1; or
   (c) nucleotides 100 to 2157 of SEQ ID NO:3; or
   (d) a polynucleotide sequence encoding a polypeptide comprising SEQ ID NO:2; or
   (e) a polynucleotide sequence encoding a polypeptide comprising amino acids 34 to 719 of SEQ ID NO:2,
   under conditions which allow for expression of the polynucleotide and, optionally, recovering the encoded polypeptide from the cell or culture medium.

9. An enzyme composition comprising the polypeptide according to claim 6 and one or more components selected from the group consisting of: milk powder, gluten, granulated fat, an additional enzyme, an amino acid, a salt, an oxidant, a reducing agent, an emulsifier, a gum, a flavour, an acid, a starch, a modified starch, gluten, a humectant, and a preservative.

10. An enzyme composition according to claim 9, wherein the additional enzyme is a lipolytic enzyme.

11. An enzyme composition according to claim 10, wherein the lipolytic enzyme is a galactolipase.

12. An enzyme composition according to claim 10, wherein the lipolytic enzyme is a phospholipase.

13. An enzyme composition according to claim 10, wherein the lipolytic enzyme is an enzyme having both phospholipase and galactolipase activity.

14. A method to prepare a dough comprising combining the polypeptide according to claim 6 and at least one component selected from the group consisting of: flour, egg, water, salt, sugar, a flavour, a fat, baker's yeast, a chemical leavening system, milk, an oxidant, a reducing agent, an emulsifier, a gum, an acid, starch, modified starch, gluten, an humectant, and a preservative.

15. A method to prepare a dough comprising combining the enzyme composition according to claim 9 and at least one component selected from the group consisting of:
   flour, egg, water, salt, sugar, a flavour, a fat, baker's yeast, a chemical leavening system, milk, an oxidant, a reducing agent, an emulsifier, a gum, an acid, starch, modified starch, gluten, an humectant, and a preservative.

16. A dough comprising the polypeptide according to claim 6.

17. A method to prepare a baked product comprising baking a dough comprising the polypeptide according to claim 6.

18. A method to prepare a baked product comprising baking a dough comprising the composition according to claim 9.

19. A method according to claim 17, wherein the baked product is bread or cake.

20. A method according to claim 18, wherein the baked product is bread or cake.

21. The isolated polypeptide of claim 6, wherein the polypeptide is produced by the method comprising:
   (a) obtaining the genome of *Alicyclobacillus pohliae* NCIMB14276;
   (b) performing sequence analysis on said genome, thereby identifying in said genome a polynucleotide encoding said polypeptide;
   (c) isolating said polynucleotide;
   (d) expressing said polypeptide from said polynucleotide; and
   (e) isolating said polypeptide.

* * * * *